US012766308B2

(12) United States Patent
Vogt et al.

(10) Patent No.: US 12,766,308 B2
(45) **Date of Patent: *Oct. 20, 2026**

(54) ROTOR BEARING SYSTEM

(71) Applicant: KARDION GMBH, Stuttgart (DE)

(72) Inventors: Andreas Vogt, Renningen (DE); Ingo Stotz, Ditzingen (DE); Johannes Bette, Leonberg (DE); Armin Schuelke, Aidlingen (DE); Xiang Li, Stuttgart (DE); Uwe Vollmer, Sindelfingen (DE); David Minzenmay, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 341 days.

This patent is subject to a terminal disclaimer.

(21) Appl. No.: 18/654,385

(22) Filed: May 3, 2024

(65) Prior Publication Data

US 2024/0277998 A1 Aug. 22, 2024

Related U.S. Application Data

(63) Continuation of application No. 17/054,884, filed as application No. PCT/EP2019/062746 on May 16, 2019, now Pat. No. 12,005,248.

(30) Foreign Application Priority Data

May 16, 2018 (DE) ..................... 10 2018 207 611.1

(51) Int. Cl.
*A61M 60/82* (2021.01)
*A61M 60/178* (2021.01)
(Continued)

(52) U.S. Cl.
CPC .......... *A61M 60/82* (2021.01); *A61M 60/178* (2021.01); *A61M 60/216* (2021.01);
(Continued)

(58) Field of Classification Search
CPC .. A61M 60/82; A61M 60/178; A61M 60/216; A61M 60/419; A61M 60/824;
(Continued)

(56) References Cited

U.S. PATENT DOCUMENTS 2,254,698 A 9/1941 Hansen, Jr.
2,310,923 A 2/1943 Bean
(Continued)

FOREIGN PATENT DOCUMENTS

AU 7993698 2/1999
AU 2002308409 12/2005
(Continued)

OTHER PUBLICATIONS

"ABMD—Taking a Closer Look at Impella ECP as the Pivotal Trial Gets Underway", Guggenheim, Press Release, Mar. 29, 2022, pp. 4.
(Continued)

*Primary Examiner* — Mark A Laurenzi
*Assistant Examiner* — Benjamin Doyle
(74) *Attorney, Agent, or Firm* — Knobbe, Martens, Olson & Bear, LLP

(57) ABSTRACT

The invention relates to a rotor bearing system (1). Said system comprises a housing (80) in which a first permanent magnet (30) is mounted such that it can rotate about a first axis (105). A rotor (70) for conveying a liquid comprises a second hollow-cylindrical permanent magnet (40), which is mounted such that it can rotate about a second axis. The first permanent magnet (30) and the second permanent magnet (40) overlap axially at least partially, wherein the first permanent magnet (30) is disposed offset relative to the second permanent magnet (40). In the axial overlap region (160) of the first permanent magnet (30) and the second permanent magnet (40), the housing (80) is positioned between the two permanent magnets (30, 40). A first bearing
(Continued)

(20) is configured for the relative axial positioning of the rotor (70) and the housing (80) with respect to one another and for receiving an axial force resulting from the arrangement of the first permanent magnet (30) and the second permanent magnet (40), and a second bearing (10) and a third bearing (90) are configured for receiving radial forces and for positioning the axis of rotation of the second permanent magnet (40).

16 Claims, 4 Drawing Sheets

(51) Int. Cl.

| | |
|---|---|
| ***A61M 60/216*** | (2021.01) |
| ***A61M 60/419*** | (2021.01) |
| ***A61M 60/824*** | (2021.01) |
| ***A61M 60/825*** | (2021.01) |
| ***F04D 3/00*** | (2006.01) |
| ***F04D 29/048*** | (2006.01) |
| ***F04D 29/18*** | (2006.01) |
| ***F16C 17/10*** | (2006.01) |
| ***H02K 7/08*** | (2006.01) |
| ***H02K 16/00*** | (2006.01) |

(52) U.S. Cl.
CPC ........ *A61M 60/419* (2021.01); *A61M 60/824* (2021.01); *A61M 60/825* (2021.01); *F04D 3/00* (2013.01); *F04D 29/048* (2013.01); *F04D 29/181* (2013.01); *F16C 17/10* (2013.01); *H02K 7/088* (2013.01); *H02K 16/005* (2013.01); *F16C 2316/18* (2013.01)

(58) Field of Classification Search
CPC ....... A61M 60/825; A61M 60/13; F04D 3/00; F04D 29/048; F04D 29/181; F04D 13/0606; F04D 29/0467; F16C 17/10; F16C 2316/18; F16C 17/26; H02K 7/088; H02K 16/005
USPC ................................ 417/423.1, 420; 415/900
See application file for complete search history.

(56) References Cited

U.S. PATENT DOCUMENTS

| | | | |
|---|---|---|---|
| 3,085,407 | A | 4/1963 | Tomlinson |
| 3,505,987 | A | 4/1970 | Heilman |
| 3,568,659 | A | 3/1971 | Karnegis |
| 3,614,181 | A | 10/1971 | Meeks |
| 3,747,998 | A | 7/1973 | Klein et al. |
| 3,807,813 | A | 4/1974 | Milligan |
| 3,995,617 | A | 12/1976 | Watkins et al. |
| 4,115,040 | A | 9/1978 | Knorr |
| 4,245,622 | A | 1/1981 | Hutchins, IV |
| 4,471,252 | A | 9/1984 | West |
| 4,522,194 | A | 6/1985 | Normann |
| 4,625,712 | A | 12/1986 | Wampler |
| 4,643,641 | A | 2/1987 | Clausen et al. |
| 4,682,981 | A | 7/1987 | Suzuki |
| 4,753,221 | A | 6/1988 | Kensey et al. |
| 4,779,614 | A | 10/1988 | Moise |
| 4,785,795 | A | 11/1988 | Singh et al. |
| 4,817,586 | A | 4/1989 | Wampler |
| 4,846,152 | A | 7/1989 | Wampler et al. |
| 4,888,011 | A | 12/1989 | Kung et al. |
| 4,889,131 | A | 12/1989 | Salem et al. |
| 4,895,557 | A | 1/1990 | Moise et al. |
| 4,896,754 | A | 1/1990 | Carlson et al. |
| 4,902,272 | A | 2/1990 | Milder et al. |
| 4,908,012 | A | 3/1990 | Moise et al. |
| 4,927,407 | A | 5/1990 | Dorman |
| 4,943,275 | A | 7/1990 | Stricker |
| 4,944,722 | A | 7/1990 | Carriker et al. |
| 4,968,300 | A | 11/1990 | Moutafis et al. |
| 4,971,768 | A | 11/1990 | Ealba |
| 4,985,014 | A | 1/1991 | Orejola |
| 5,044,897 | A | 9/1991 | Dorman |
| 5,061,256 | A | 10/1991 | Wampler |
| 5,089,016 | A | 2/1992 | Millner et al. |
| 5,090,957 | A | 2/1992 | Moutafis et al. |
| 5,112,292 | A | 5/1992 | Hwang et al. |
| 5,112,349 | A | 5/1992 | Summers et al. |
| 5,116,305 | A | 5/1992 | Milder et al. |
| 5,195,877 | A | 3/1993 | Kletschka |
| 5,290,227 | A | 3/1994 | Pasque |
| 5,297,940 | A | 3/1994 | Buse |
| 5,309,055 | A | 5/1994 | Leupold |
| 5,313,765 | A | 5/1994 | Martin |
| 5,344,443 | A | 9/1994 | Palma et al. |
| 5,354,271 | A | 10/1994 | Voda |
| 5,376,114 | A | 12/1994 | Jarvik |
| 5,399,145 | A | 3/1995 | Ito et al. |
| 5,405,383 | A | 4/1995 | Barr |
| 5,443,503 | A | 8/1995 | Yamane |
| 5,456,715 | A | 10/1995 | Liotta |
| 5,527,159 | A | 6/1996 | Bozeman, Jr. et al. |
| 5,599,173 | A | 2/1997 | Chen et al. |
| 5,613,935 | A | 3/1997 | Jarvik |
| 5,695,471 | A | 12/1997 | Wampler |
| 5,702,430 | A | 12/1997 | Larson, Jr. et al. |
| 5,720,771 | A | 2/1998 | Snell |
| 5,746,709 | A | 5/1998 | Rom et al. |
| 5,749,855 | A | 5/1998 | Reitan |
| 5,752,976 | A | 5/1998 | Duffin et al. |
| 5,766,207 | A | 6/1998 | Potter et al. |
| 5,831,365 | A | 11/1998 | Keim et al. |
| 5,888,241 | A | 3/1999 | Jarvik |
| 5,888,242 | A | 3/1999 | Antaki et al. |
| 5,904,646 | A | 5/1999 | Jarvik |
| 5,911,685 | A | 6/1999 | Siess et al. |
| 5,921,913 | A | 7/1999 | Siess |
| 5,964,694 | A | 10/1999 | Siess et al. |
| 6,001,056 | A | 12/1999 | Jassawalla et al. |
| 6,007,478 | A | 12/1999 | Siess et al. |
| 6,018,208 | A | 1/2000 | Maher et al. |
| 6,050,975 | A | 4/2000 | Poirier |
| 6,071,093 | A | 6/2000 | Hart |
| 6,116,862 | A | 9/2000 | Rau et al. |
| 6,123,659 | A | 9/2000 | le Blanc et al. |
| 6,135,710 | A | 10/2000 | Araki et al. |
| 6,149,405 | A | 11/2000 | Abe et al. |
| 6,155,969 | A | 12/2000 | Schima et al. |
| 6,158,984 | A | 12/2000 | Cao et al. |
| 6,161,838 | A | 12/2000 | Balsells |
| 6,176,848 | B1 | 1/2001 | Rau et al. |
| 6,186,665 | B1 | 2/2001 | Maher et al. |
| 6,210,318 | B1 | 4/2001 | Lederman |
| 6,217,541 | B1 | 4/2001 | Yu |
| 6,220,832 | B1 | 4/2001 | Schob |
| 6,227,820 | B1 | 5/2001 | Jarvik |
| 6,245,007 | B1 | 6/2001 | Bedingham et al. |
| 6,254,359 | B1 | 7/2001 | Aber |
| 6,264,205 | B1 | 7/2001 | Balsells |
| 6,264,601 | B1 | 7/2001 | Jassawalla et al. |
| 6,264,645 | B1 | 7/2001 | Jonkman |
| 6,293,752 | B1 | 9/2001 | Clague et al. |
| 6,351,048 | B1 | 2/2002 | Schob et al. |
| 6,361,292 | B1 | 3/2002 | Chang et al. |
| 6,432,136 | B1 | 8/2002 | Weiss et al. |
| 6,445,956 | B1 | 9/2002 | Laird et al. |
| 6,447,266 | B2 | 9/2002 | Antaki et al. |
| 6,527,698 | B1 | 3/2003 | Kung et al. |
| 6,530,876 | B1 | 3/2003 | Spence |
| 6,533,716 | B1 | 3/2003 | Schmitz-Rode et al. |
| 6,540,658 | B1 | 4/2003 | Fasciano et al. |
| 6,544,216 | B1 | 4/2003 | Sammler et al. |
| 6,579,257 | B1 | 6/2003 | Elgas et al. |
| 6,592,620 | B1 | 7/2003 | Lancisi et al. |
| 6,595,743 | B1 | 7/2003 | Kazatchkov et al. |
| 6,607,368 | B1 | 8/2003 | Ross et al. |

(56) References Cited

U.S. PATENT DOCUMENTS

| | | | |
|---|---|---|---|
| 6,623,475 | B1 | 9/2003 | Siess |
| 6,719,791 | B1 | 4/2004 | Nüsser et al. |
| 6,794,789 | B2 | 9/2004 | Siess et al. |
| 6,841,910 | B2 | 1/2005 | Gery |
| 6,879,126 | B2 | 4/2005 | Paden et al. |
| 6,912,423 | B2 | 6/2005 | Ley et al. |
| 6,942,611 | B2 | 9/2005 | Siess |
| 6,949,066 | B2 | 9/2005 | Bearnson et al. |
| 6,969,345 | B2 | 11/2005 | Jassawalla et al. |
| 7,011,620 | B1 | 3/2006 | Siess |
| 7,014,620 | B2 | 3/2006 | Kim |
| 7,022,100 | B1 | 4/2006 | Aboul-Hosn et al. |
| 7,027,875 | B2 | 4/2006 | Siess et al. |
| 7,070,398 | B2 | 7/2006 | Olsen et al. |
| 7,070,555 | B2 | 7/2006 | Siess |
| 7,083,588 | B1 | 8/2006 | Shmulewitz et al. |
| 7,144,364 | B2 | 12/2006 | Barbut et al. |
| 7,160,243 | B2 | 1/2007 | Medvedev |
| 7,238,151 | B2 | 7/2007 | Frazier |
| 7,241,257 | B1 | 7/2007 | Ainsworth et al. |
| 7,264,606 | B2 | 9/2007 | Jarvik et al. |
| 7,393,181 | B2 | 7/2008 | McBride et al. |
| 7,436,145 | B2 | 10/2008 | Gauthier et al. |
| 7,462,019 | B1 | 12/2008 | Allarie et al. |
| 7,479,102 | B2 | 1/2009 | Jarvik |
| 7,502,648 | B2 | 3/2009 | Okubo et al. |
| 7,736,296 | B2 | 6/2010 | Siess et al. |
| 7,762,941 | B2 | 7/2010 | Jarvik |
| 7,798,952 | B2 | 9/2010 | Tansley et al. |
| 7,841,976 | B2 | 11/2010 | McBride et al. |
| 7,850,593 | B2 | 12/2010 | Vincent et al. |
| 7,878,967 | B1 | 2/2011 | Khanal |
| 7,914,436 | B1 | 3/2011 | Kung |
| 7,934,909 | B2 | 5/2011 | Nuesser et al. |
| 7,959,551 | B2 | 6/2011 | Jarvik |
| 7,963,905 | B2 | 6/2011 | Salmonsen et al. |
| 7,998,190 | B2 | 8/2011 | Gharib et al. |
| 8,012,079 | B2 | 9/2011 | Delgado, III |
| 8,075,472 | B2 | 12/2011 | Zilbershlag et al. |
| 8,088,059 | B2 | 1/2012 | Jarvik |
| 8,114,008 | B2 | 2/2012 | Hidaka et al. |
| 8,123,669 | B2 | 2/2012 | Siess et al. |
| RE43,299 | E | 4/2012 | Siess |
| 8,152,845 | B2 | 4/2012 | Bourque |
| 8,177,703 | B2 | 5/2012 | Smith et al. |
| 8,216,122 | B2 | 7/2012 | Kung |
| 8,371,997 | B2 | 2/2013 | Shifflette |
| 8,376,926 | B2 | 2/2013 | Benkowsi et al. |
| 8,382,695 | B1 | 2/2013 | Patel |
| 8,388,565 | B2 | 3/2013 | Shifflette |
| 8,419,609 | B2 | 4/2013 | Shambaugh, Jr. et al. |
| 8,449,443 | B2 | 5/2013 | Rodefeld et al. |
| 8,480,555 | B2 | 7/2013 | Kung |
| 8,485,961 | B2 | 7/2013 | Campbell et al. |
| 8,512,012 | B2 | 8/2013 | Akdis et al. |
| 8,535,211 | B2 | 9/2013 | Campbell et al. |
| 8,545,380 | B2 | 10/2013 | Farnan et al. |
| 8,562,508 | B2 | 10/2013 | Dague et al. |
| 8,585,572 | B2 | 11/2013 | Mehmanesh |
| 8,591,393 | B2 | 11/2013 | Walters et al. |
| 8,591,538 | B2 | 11/2013 | Gellman |
| 8,591,539 | B2 | 11/2013 | Gellman |
| 8,597,170 | B2 | 12/2013 | Walters et al. |
| 8,617,239 | B2 | 12/2013 | Reitan |
| 8,622,949 | B2 | 1/2014 | Zafirelis et al. |
| 8,641,594 | B2 | 2/2014 | LaRose et al. |
| 8,657,875 | B2 | 2/2014 | Kung et al. |
| 8,684,362 | B2 | 4/2014 | Balsells et al. |
| 8,684,904 | B2 | 4/2014 | Campbell et al. |
| 8,690,749 | B1 | 4/2014 | Nunez |
| 8,721,517 | B2 | 5/2014 | Zeng et al. |
| 8,727,959 | B2 | 5/2014 | Reitan et al. |
| 8,731,664 | B2 | 5/2014 | Foster et al. |
| 8,734,331 | B2 | 5/2014 | Evans et al. |
| 8,814,933 | B2 | 8/2014 | Siess |
| 8,849,398 | B2 | 9/2014 | Evans |
| 8,864,642 | B2 | 10/2014 | Scheckel |
| 8,864,643 | B2 | 10/2014 | Reichenbach et al. |
| 8,864,644 | B2 | 10/2014 | Yomtov |
| 8,882,477 | B2 | 11/2014 | Fritz, IV et al. |
| 8,888,728 | B2 | 11/2014 | Aboul-Hosn et al. |
| 8,894,387 | B2 | 11/2014 | White |
| 8,897,873 | B2 | 11/2014 | Schima et al. |
| 8,900,060 | B2 | 12/2014 | Liebing |
| 8,900,115 | B2 | 12/2014 | Bolling et al. |
| 8,932,246 | B2 | 1/2015 | Ferrari |
| 8,992,406 | B2 | 3/2015 | Corbett |
| 8,992,407 | B2 | 3/2015 | Smith et al. |
| 9,028,216 | B2 | 5/2015 | Schumacher et al. |
| 9,028,392 | B2 | 5/2015 | Shifflette |
| 9,033,863 | B2 | 5/2015 | Jarvik |
| 9,091,271 | B2 | 7/2015 | Bourque |
| 9,138,518 | B2 | 9/2015 | Campbell et al. |
| 9,144,638 | B2 | 9/2015 | Zimmermann et al. |
| 9,162,017 | B2 | 10/2015 | Evans et al. |
| 9,192,705 | B2 | 11/2015 | Yanai et al. |
| 9,199,020 | B2 | 12/2015 | Siess |
| 9,265,870 | B2 | 2/2016 | Reichenbach et al. |
| 9,297,735 | B2 | 3/2016 | Graichen et al. |
| 9,314,556 | B2 | 4/2016 | Tuseth |
| 9,327,067 | B2 | 5/2016 | Zeng et al. |
| 9,327,068 | B2 | 5/2016 | Aboul-Hosn et al. |
| 9,345,824 | B2 | 5/2016 | Mohl et al. |
| 9,370,613 | B2 | 6/2016 | Hsu et al. |
| 9,371,826 | B2 | 6/2016 | Yanai et al. |
| 9,381,286 | B2 | 7/2016 | Spence et al. |
| 9,421,311 | B2 | 8/2016 | Tanner et al. |
| 9,433,713 | B2 | 9/2016 | Corbett et al. |
| 9,440,013 | B2 | 9/2016 | Dowling et al. |
| 9,474,840 | B2 | 10/2016 | Siess |
| 9,486,566 | B2 | 11/2016 | Siess |
| 9,492,601 | B2 | 11/2016 | Casas et al. |
| 9,533,084 | B2 | 1/2017 | Siess et al. |
| 9,539,378 | B2 | 1/2017 | Tuseth |
| 9,550,017 | B2 | 1/2017 | Spanier et al. |
| 9,555,173 | B2 | 1/2017 | Spanier |
| 9,555,175 | B2 | 1/2017 | Bulent et al. |
| 9,556,873 | B2 | 1/2017 | Yanai et al. |
| 9,561,313 | B2 | 2/2017 | Taskin |
| 9,561,314 | B2 | 2/2017 | Aboul-Hosn et al. |
| 9,579,433 | B2 | 2/2017 | LaRose et al. |
| 9,585,991 | B2 | 3/2017 | Spence |
| 9,592,397 | B2 | 3/2017 | Hansen et al. |
| 9,616,157 | B2 | 4/2017 | Akdis |
| 9,623,162 | B2 | 4/2017 | Graham et al. |
| 9,623,163 | B1 | 4/2017 | Fischi |
| 9,636,442 | B2 | 5/2017 | Karmon et al. |
| 9,669,144 | B2 | 6/2017 | Spanier et al. |
| 9,675,738 | B2 | 6/2017 | Tanner et al. |
| 9,675,739 | B2 | 6/2017 | Tanner et al. |
| 9,675,740 | B2 | 6/2017 | Zeng et al. |
| 9,682,180 | B2 | 6/2017 | Hoarau et al. |
| 9,717,833 | B2 | 8/2017 | McBride et al. |
| 9,731,058 | B2 | 8/2017 | Siebenhaar et al. |
| 9,759,222 | B2 | 9/2017 | Zimmermann et al. |
| 9,770,543 | B2 | 9/2017 | Tanner et al. |
| 9,789,238 | B2 | 10/2017 | Aboul-Hosn et al. |
| 9,801,990 | B2 | 10/2017 | Lynch |
| 9,814,813 | B2 | 11/2017 | Corbett |
| 9,821,100 | B2 | 11/2017 | Corbett et al. |
| 9,833,550 | B2 | 12/2017 | Siess |
| 9,849,223 | B2 | 12/2017 | LaRose |
| 9,872,948 | B2 | 1/2018 | Siess |
| 9,878,087 | B2 | 1/2018 | Richardson et al. |
| 9,907,890 | B2 | 3/2018 | Muller |
| 9,919,087 | B2 | 3/2018 | Pfeffer et al. |
| 9,950,101 | B2 | 4/2018 | Smith et al. |
| 9,968,719 | B2 | 5/2018 | Colella |
| 9,999,714 | B2 | 6/2018 | Spanier et al. |
| 10,029,037 | B2 | 7/2018 | Muller et al. |
| 10,123,875 | B2 | 11/2018 | Wildhirt et al. |
| 10,124,102 | B2 | 11/2018 | Bulent et al. |
| 10,130,742 | B2 | 11/2018 | Tuseth |
| 10,149,932 | B2 | 12/2018 | McBride et al. |

(56) References Cited

U.S. PATENT DOCUMENTS

| | | | |
|---|---|---|---|
| 10,179,197 | B2 | 1/2019 | Kaiser et al. |
| 10,201,645 | B2 | 2/2019 | Muller |
| 10,207,038 | B2 | 2/2019 | Neumann |
| 10,220,129 | B2 | 3/2019 | Ayre et al. |
| 10,232,099 | B2 | 3/2019 | Peters et al. |
| 10,238,782 | B2 | 3/2019 | Barry |
| 10,238,783 | B2 | 3/2019 | Aboul-Hosn et al. |
| 10,251,986 | B2 | 4/2019 | Larose et al. |
| 10,279,093 | B2 | 5/2019 | Reichenbach et al. |
| 10,293,090 | B2 | 5/2019 | Bonde et al. |
| 10,300,185 | B2 | 5/2019 | Aboul-Hosn et al. |
| 10,300,249 | B2 | 5/2019 | Tao et al. |
| 10,322,217 | B2 | 6/2019 | Spence |
| 10,342,906 | B2 | 7/2019 | D'Ambrosio et al. |
| 10,357,598 | B2 | 7/2019 | Aboul-Hosn et al. |
| 10,361,617 | B2 | 7/2019 | Mueller et al. |
| 10,371,150 | B2 | 8/2019 | Wu et al. |
| 10,376,162 | B2 | 8/2019 | Edelman et al. |
| 10,420,869 | B2 | 9/2019 | Cornen |
| 10,434,232 | B2 | 10/2019 | Wu et al. |
| 10,449,275 | B2 | 10/2019 | Corbett |
| 10,449,279 | B2 | 10/2019 | Muller |
| 10,478,538 | B2 | 11/2019 | Scheckel et al. |
| 10,478,539 | B2 | 11/2019 | Pfeffer et al. |
| 10,478,542 | B2 | 11/2019 | Jahangir |
| 10,500,323 | B2 | 12/2019 | Heuring et al. |
| 10,512,537 | B2 | 12/2019 | Corbett et al. |
| 10,525,178 | B2 | 1/2020 | Zeng |
| 10,537,670 | B2 | 1/2020 | Tuseth et al. |
| 10,537,672 | B2 | 1/2020 | Tuseth et al. |
| 10,557,475 | B2 | 2/2020 | Roehn |
| 10,561,771 | B2 | 2/2020 | Heilman et al. |
| 10,561,772 | B2 | 2/2020 | Schumacher |
| 10,576,191 | B2 | 3/2020 | LaRose |
| 10,584,589 | B2 | 3/2020 | Schumacher et al. |
| 10,589,012 | B2 | 3/2020 | Toellner et al. |
| 10,589,013 | B2 | 3/2020 | Bourque |
| 10,610,626 | B2 | 4/2020 | Spanier et al. |
| 10,617,808 | B2 | 4/2020 | Hastie et al. |
| 10,632,241 | B2 | 4/2020 | Schenck et al. |
| 10,639,460 | B2 | 5/2020 | Nitzan et al. |
| 10,653,871 | B2 | 5/2020 | Nitzan et al. |
| 10,660,998 | B2 | 5/2020 | Hodges |
| 10,662,967 | B2 | 5/2020 | Scheckel |
| 10,668,195 | B2 | 6/2020 | Flores |
| 10,669,855 | B2 | 6/2020 | Toellner et al. |
| 10,722,631 | B2 | 7/2020 | Salahieh et al. |
| 10,773,002 | B2 | 9/2020 | Siess et al. |
| 10,780,208 | B2 | 9/2020 | Siess et al. |
| 10,808,704 | B2 | 10/2020 | Siess et al. |
| 10,814,053 | B2 | 10/2020 | Throckmorton et al. |
| 10,857,273 | B2 | 12/2020 | Hodges et al. |
| 10,857,274 | B2 | 12/2020 | Alexander et al. |
| 10,864,308 | B2 | 12/2020 | Muller et al. |
| 10,926,069 | B2 | 2/2021 | Nitzan et al. |
| 11,027,114 | B2 | 6/2021 | D'Ambrosio et al. |
| 11,033,729 | B2 | 6/2021 | Scheckel et al. |
| 11,045,638 | B2 | 6/2021 | Keenan et al. |
| 11,058,863 | B2 | 7/2021 | Demou |
| 11,058,865 | B2 | 7/2021 | Fitzgerald et al. |
| 11,065,434 | B2 | 7/2021 | Egler et al. |
| 11,092,158 | B2 | 8/2021 | Siess et al. |
| 11,097,092 | B2 | 8/2021 | Siess et al. |
| 11,103,689 | B2 | 8/2021 | Siess et al. |
| 11,103,690 | B2 | 8/2021 | Epple |
| 11,107,626 | B2 | 8/2021 | Siess et al. |
| 11,116,959 | B2 | 9/2021 | Alexander et al. |
| 11,123,538 | B2 | 9/2021 | Epple et al. |
| 11,123,539 | B2 | 9/2021 | Pfeffer et al. |
| 11,123,541 | B2 | 9/2021 | Corbett et al. |
| 11,129,978 | B2 | 9/2021 | Pfeffer et al. |
| 11,141,579 | B2 | 10/2021 | Steingräber |
| 11,160,970 | B2 | 11/2021 | Muller et al. |
| 11,167,124 | B2 | 11/2021 | Pfeffer et al. |
| 11,173,297 | B2 | 11/2021 | Muller |
| 11,179,557 | B2 | 11/2021 | Georges et al. |
| 11,185,678 | B2 | 11/2021 | Smith et al. |
| 11,185,680 | B2 | 11/2021 | Tuval et al. |
| 11,191,944 | B2 | 12/2021 | Tuval et al. |
| 11,197,989 | B2 | 12/2021 | Arslan et al. |
| 11,202,901 | B2 | 12/2021 | Barry |
| 11,219,756 | B2 | 1/2022 | Tanner et al. |
| 11,229,786 | B2 | 1/2022 | Zeng et al. |
| 11,235,138 | B2 | 2/2022 | Gross-Hardt et al. |
| 11,235,140 | B2 | 2/2022 | Siess et al. |
| 11,241,568 | B2 | 2/2022 | Keenan et al. |
| 11,241,569 | B2 | 2/2022 | Delgado, III |
| 11,253,693 | B2 | 2/2022 | Pfeffer et al. |
| 11,260,212 | B2 | 3/2022 | Tuval et al. |
| 11,260,213 | B2 | 3/2022 | Zeng et al. |
| 11,260,215 | B2 | 3/2022 | Scheckel et al. |
| 11,273,300 | B2 | 3/2022 | Schafir |
| 11,273,301 | B2 | 3/2022 | Pfeffer et al. |
| 11,278,711 | B2 | 3/2022 | Liebing |
| 11,280,345 | B2 | 3/2022 | Bredenbreuker et al. |
| 11,285,309 | B2 | 3/2022 | Tuval et al. |
| 11,291,824 | B2 | 4/2022 | Schwammenthal et al. |
| 11,291,825 | B2 | 4/2022 | Tuval et al. |
| 11,291,826 | B2 | 4/2022 | Tuval et al. |
| 11,298,519 | B2 | 4/2022 | Josephy et al. |
| 11,298,520 | B2 | 4/2022 | Schwammenthal et al. |
| 11,298,521 | B2 | 4/2022 | Schwammenthal et al. |
| 11,298,523 | B2 | 4/2022 | Tuval et al. |
| 11,298,524 | B2 | 4/2022 | El Katerji et al. |
| 11,298,525 | B2 | 4/2022 | Jahangir |
| 11,305,103 | B2 | 4/2022 | Larose et al. |
| 11,305,105 | B2 | 4/2022 | Corbett et al. |
| 11,311,711 | B2 | 4/2022 | Casas et al. |
| 11,311,712 | B2 | 4/2022 | Zeng et al. |
| 11,313,228 | B2 | 4/2022 | Schumacher et al. |
| D951,435 | S | 5/2022 | Motomura et al. |
| 11,318,295 | B2 | 5/2022 | Reyes et al. |
| 11,324,940 | B2 | 5/2022 | Earles et al. |
| 11,324,941 | B2 | 5/2022 | Xu et al. |
| 11,331,465 | B2 | 5/2022 | Epple |
| 11,331,466 | B2 | 5/2022 | Keen et al. |
| 11,331,467 | B2 | 5/2022 | King et al. |
| 11,331,470 | B2 | 5/2022 | Muller et al. |
| 11,338,124 | B2 | 5/2022 | Pfeffer et al. |
| 11,338,125 | B2 | 5/2022 | Liu et al. |
| 11,344,716 | B2 | 5/2022 | Taskin |
| 11,344,717 | B2 | 5/2022 | Kallenbach et al. |
| 11,351,356 | B2 | 6/2022 | Mohl |
| 11,351,357 | B2 | 6/2022 | Mohl |
| 11,351,359 | B2 | 6/2022 | Clifton et al. |
| 11,357,967 | B2 | 6/2022 | Zeng et al. |
| 11,364,373 | B2 | 6/2022 | Corbett et al. |
| 11,368,081 | B2 | 6/2022 | Vogt et al. |
| 11,369,785 | B2 | 6/2022 | Callaway et al. |
| 11,369,786 | B2 | 6/2022 | Menon et al. |
| 11,376,415 | B2 | 7/2022 | Mohl |
| 11,389,639 | B2 | 7/2022 | Casas |
| 11,389,641 | B2 | 7/2022 | Nguyen et al. |
| 11,413,443 | B2 | 8/2022 | Hodges et al. |
| 11,413,446 | B2 | 8/2022 | Siess et al. |
| 11,415,150 | B2 | 8/2022 | Richert et al. |
| 11,421,701 | B2 | 8/2022 | Schumacher et al. |
| 11,428,236 | B2 | 8/2022 | McBride et al. |
| 11,433,168 | B2 | 9/2022 | Wu et al. |
| 11,434,921 | B2 | 9/2022 | McBride et al. |
| 11,434,922 | B2 | 9/2022 | Roehn |
| 11,446,481 | B2 | 9/2022 | Wolman et al. |
| 11,446,482 | B2 | 9/2022 | Kirchhoff et al. |
| 11,452,859 | B2 | 9/2022 | Earles et al. |
| 11,460,030 | B2 | 10/2022 | Shambaugh et al. |
| 11,471,662 | B2 | 10/2022 | Akkerman et al. |
| 11,471,663 | B2 | 10/2022 | Tuval et al. |
| 11,471,665 | B2 | 10/2022 | Clifton et al. |
| 11,478,627 | B2 | 10/2022 | Siess et al. |
| 11,478,628 | B2 | 10/2022 | Muller et al. |
| 11,478,629 | B2 | 10/2022 | Harjes et al. |
| 11,484,698 | B2 | 11/2022 | Radman |
| 11,484,699 | B2 | 11/2022 | Tuval et al. |
| 11,486,400 | B2 | 11/2022 | Schumacher |

(56) References Cited

U.S. PATENT DOCUMENTS

| | | | |
|---|---|---|---|
| 11,491,320 | B2 | 11/2022 | Siess |
| 11,491,322 | B2 | 11/2022 | Muller et al. |
| 11,497,896 | B2 | 11/2022 | Tanner et al. |
| 11,497,906 | B2 | 11/2022 | Grace et al. |
| 11,511,101 | B2 | 11/2022 | Hastie et al. |
| 11,511,103 | B2 | 11/2022 | Salahieh et al. |
| 11,511,104 | B2 | 11/2022 | Dur et al. |
| 11,517,726 | B2 | 12/2022 | Siess et al. |
| 11,517,736 | B2 | 12/2022 | Earles et al. |
| 11,517,737 | B2 | 12/2022 | Struthers et al. |
| 11,517,738 | B2 | 12/2022 | Wisniewski |
| 11,517,739 | B2 | 12/2022 | Toellner |
| 11,517,740 | B2 | 12/2022 | Agarwa et al. |
| 11,524,137 | B2 | 12/2022 | Jahangir |
| 11,524,153 | B2 | 12/2022 | Alexander et al. |
| 11,524,165 | B2 | 12/2022 | Tan et al. |
| 11,529,062 | B2 | 12/2022 | Moyer et al. |
| 11,534,596 | B2 | 12/2022 | Schafir et al. |
| 11,565,103 | B2 | 1/2023 | Farago et al. |
| 11,569,015 | B2 | 1/2023 | Mourran et al. |
| 11,572,879 | B2 | 2/2023 | Mohl |
| 11,577,067 | B2 | 2/2023 | Breidall et al. |
| 11,577,068 | B2 | 2/2023 | Spence et al. |
| 11,583,659 | B2 | 2/2023 | Pfeffer et al. |
| 11,583,670 | B2 | 2/2023 | Pfeifer et al. |
| 11,583,671 | B2 | 2/2023 | Nguyen et al. |
| 11,583,672 | B2 | 2/2023 | Weber et al. |
| 11,585,346 | B2 | 2/2023 | Bareis et al. |
| 11,590,336 | B2 | 2/2023 | Harjes et al. |
| 11,590,337 | B2 | 2/2023 | Granegger et al. |
| 11,590,338 | B2 | 2/2023 | Barry |
| 11,592,028 | B2 | 2/2023 | Schumacher et al. |
| 11,596,727 | B2 | 3/2023 | Siess et al. |
| 11,602,627 | B2 | 3/2023 | Leonhardt |
| 11,617,876 | B2 | 4/2023 | Scheckel et al. |
| 11,628,293 | B2 | 4/2023 | Gandhi et al. |
| 11,632,015 | B2 | 4/2023 | Sconzert et al. |
| 11,633,586 | B2 | 4/2023 | Tanner et al. |
| 11,638,813 | B2 | 5/2023 | West |
| 11,639,722 | B2 | 5/2023 | Medvedev et al. |
| 11,642,511 | B2 | 5/2023 | Delgado, III |
| 11,648,387 | B2 | 5/2023 | Schwammenthal et al. |
| 11,648,388 | B2 | 5/2023 | Siess et al. |
| 11,648,389 | B2 | 5/2023 | Wang et al. |
| 11,648,390 | B2 | 5/2023 | Spanier et al. |
| 11,648,391 | B2 | 5/2023 | Schwammenthal et al. |
| 11,648,392 | B2 | 5/2023 | Tuval et al. |
| 11,648,393 | B2 | 5/2023 | Taskin et al. |
| 11,654,273 | B2 | 5/2023 | Granegger et al. |
| 11,654,275 | B2 | 5/2023 | Brandt |
| 11,654,276 | B2 | 5/2023 | Fitzgerald et al. |
| 11,660,441 | B2 | 5/2023 | Fitzgerald et al. |
| 11,666,747 | B2 | 6/2023 | Tuval et al. |
| 11,666,748 | B2 | 6/2023 | Kronstedt et al. |
| 11,668,321 | B2 | 6/2023 | Richert et al. |
| 11,674,517 | B2 | 6/2023 | Mohl |
| 11,679,234 | B2 | 6/2023 | King et al. |
| 11,679,249 | B2 | 6/2023 | Scheckel et al. |
| 11,679,250 | B2 | 6/2023 | Alexander et al. |
| 11,684,275 | B2 | 6/2023 | Tuval et al. |
| 11,684,769 | B2 | 6/2023 | Harjes et al. |
| 11,690,521 | B2 | 7/2023 | Tuval et al. |
| 11,690,996 | B2 | 7/2023 | Siess et al. |
| 11,697,016 | B2 | 7/2023 | Epple |
| 11,701,510 | B2 | 7/2023 | Demou |
| 11,702,938 | B2 | 7/2023 | Schumacher et al. |
| 11,703,064 | B2 | 7/2023 | Bredenbreuker et al. |
| 11,708,833 | B2 | 7/2023 | McBride et al. |
| 11,744,987 | B2 | 9/2023 | Siess et al. |
| 11,745,005 | B2 | 9/2023 | Delgado, III |
| 11,746,906 | B1 | 9/2023 | Balta et al. |
| 11,752,322 | B2 | 9/2023 | Aboulhosn et al. |
| 11,752,323 | B2 | 9/2023 | Edwards et al. |
| 11,754,075 | B2 | 9/2023 | Schuelke et al. |
| 11,754,077 | B1 | 9/2023 | Mohl |
| 11,759,612 | B2 | 9/2023 | Tanner et al. |
| 11,759,622 | B2 | 9/2023 | Siess et al. |
| 11,766,555 | B2 | 9/2023 | Matthes et al. |
| 11,771,884 | B2 | 10/2023 | Siess et al. |
| 11,771,885 | B2 | 10/2023 | Liu et al. |
| 11,779,234 | B2 | 10/2023 | Harjes et al. |
| 11,779,751 | B2 | 10/2023 | Earles et al. |
| 11,781,550 | B2 | 10/2023 | Siess et al. |
| 11,781,551 | B2 | 10/2023 | Yanai et al. |
| 11,786,386 | B2 | 10/2023 | Brady et al. |
| 11,786,700 | B2 | 10/2023 | Pfeffer et al. |
| 11,786,720 | B2 | 10/2023 | Muller |
| 11,793,994 | B2 | 10/2023 | Josephy et al. |
| 11,804,767 | B2 | 10/2023 | Vogt et al. |
| 11,806,116 | B2 | 11/2023 | Tuval et al. |
| 11,806,117 | B2 | 11/2023 | Tuval et al. |
| 11,806,517 | B2 | 11/2023 | Petersen |
| 11,806,518 | B2 | 11/2023 | Michelena et al. |
| 11,813,443 | B2 | 11/2023 | Hanson et al. |
| 11,813,444 | B2 | 11/2023 | Siess et al. |
| 11,813,445 | B2 | 11/2023 | Alexander et al. |
| 11,819,678 | B2 | 11/2023 | Siess et al. |
| 11,826,127 | B2 | 11/2023 | Casas |
| 11,833,278 | B2 | 12/2023 | Siess et al. |
| 11,833,342 | B2 | 12/2023 | Tanner et al. |
| 11,839,754 | B2 | 12/2023 | Tuval et al. |
| 11,844,592 | B2 | 12/2023 | Tuval et al. |
| 11,844,940 | B2 | 12/2023 | D'Ambrosio et al. |
| 11,850,412 | B2 | 12/2023 | Grauwinkel et al. |
| 11,850,413 | B2 | 12/2023 | Zeng et al. |
| 11,850,414 | B2 | 12/2023 | Schenck et al. |
| 11,850,415 | B2 | 12/2023 | Schwammenthal et al. |
| 11,857,743 | B2 | 1/2024 | Fantuzzi et al. |
| 11,857,777 | B2 | 1/2024 | Earles et al. |
| 11,865,238 | B2 | 1/2024 | Siess et al. |
| 11,872,384 | B2 | 1/2024 | Cotter |
| 11,883,005 | B2 | 1/2024 | Golden et al. |
| 11,883,207 | B2 | 1/2024 | El Katerji et al. |
| 11,883,310 | B2 | 1/2024 | Nolan et al. |
| 11,883,641 | B2 | 1/2024 | Dur et al. |
| 11,890,212 | B2 | 2/2024 | Gilmartin et al. |
| 11,896,482 | B2 | 2/2024 | Delaloye et al. |
| 11,898,642 | B2 | 2/2024 | Stanton et al. |
| 11,904,104 | B2 | 2/2024 | Jahangir |
| 11,911,579 | B2 | 2/2024 | Tanner et al. |
| 11,918,470 | B2 | 3/2024 | Jarral et al. |
| 11,918,496 | B2 | 3/2024 | Folan |
| 11,918,726 | B2 | 3/2024 | Siess et al. |
| 11,918,800 | B2 | 3/2024 | Muller et al. |
| 11,925,356 | B2 | 3/2024 | Anderson et al. |
| 11,925,570 | B2 | 3/2024 | Lydecker et al. |
| 11,925,794 | B2 | 3/2024 | Malkin et al. |
| 11,925,795 | B2 | 3/2024 | Muller et al. |
| 11,925,796 | B2 | 3/2024 | Tanner et al. |
| 11,925,797 | B2 | 3/2024 | Tanner et al. |
| 11,938,311 | B2 | 3/2024 | Corbett et al. |
| 11,944,805 | B2 | 4/2024 | Stotz |
| 11,957,892 | B2 | 4/2024 | Siess et al. |
| 11,980,385 | B2 | 5/2024 | Haselman |
| 11,986,604 | B2 | 5/2024 | Siess |
| 12,005,248 | B2 | 6/2024 | Vogt et al. |
| 12,011,583 | B2 | 6/2024 | Wang |
| 12,017,058 | B2 | 6/2024 | Kerkhoffs et al. |
| 12,023,476 | B2 | 7/2024 | Tuval et al. |
| 12,023,477 | B2 | 7/2024 | Siess |
| 12,053,624 | B2 | 8/2024 | Alexander et al. |
| 12,059,559 | B2 | 8/2024 | Muller et al. |
| 12,064,120 | B2 | 8/2024 | Hajjar et al. |
| 12,064,611 | B2 | 8/2024 | D'Ambrosio et al. |
| 12,064,614 | B2 | 8/2024 | Agah et al. |
| 12,064,615 | B2 | 8/2024 | Stotz et al. |
| 12,064,616 | B2 | 8/2024 | Spanier et al. |
| 12,076,544 | B2 | 9/2024 | Siess et al. |
| 12,076,549 | B2 | 9/2024 | Stotz et al. |
| 12,076,550 | B2 | 9/2024 | Edwards et al. |
| 12,078,192 | B2 | 9/2024 | Gross-Hardt et al. |
| 12,090,310 | B2 | 9/2024 | Alexander et al. |
| 12,090,314 | B2 | 9/2024 | Tuval et al. |
| 12,092,114 | B2 | 9/2024 | Siess |

(56) References Cited

U.S. PATENT DOCUMENTS 12,097,016 B2 9/2024 Goldvasser
12,102,815 B2 10/2024 Dhaliwal et al.
12,104,600 B2 10/2024 Mohl
12,107,474 B2 10/2024 Vollmer
12,117,007 B1 10/2024 Mohl
12,121,713 B2 10/2024 Calomeni et al.
12,133,976 B2 11/2024 Malone et al.
12,138,438 B2 11/2024 Alexander et al.
12,144,936 B2 11/2024 Tao et al.
12,144,976 B2 11/2024 Baumbach et al.
12,151,092 B2 11/2024 Alexander et al.
12,161,854 B2 12/2024 Earles et al.
12,161,855 B2 12/2024 Hastie et al.
12,161,857 B2 12/2024 Saul et al.
12,171,993 B2 12/2024 Higgins et al.
12,194,287 B2 1/2025 Kassel et al.
12,196,210 B2 1/2025 Siess et al.
12,201,823 B2 1/2025 Baumbach et al.
12,207,906 B2 1/2025 Tuval et al.
12,213,771 B2 2/2025 Curran et al.
12,233,251 B2 2/2025 Siess et al.
12,241,480 B2 3/2025 Corbett et al.
12,263,330 B2 4/2025 D'Ambrosio et al.
12,263,333 B2 4/2025 Stotz et al.
12,263,334 B2 4/2025 Corbett et al.
12,268,861 B2 4/2025 D'Ambrosio et al.
12,290,673 B2 5/2025 Jahangir
12,290,676 B2 5/2025 Farago et al.
12,303,678 B2 5/2025 Kerkhoffs et al.
12,303,680 B2 5/2025 Siess et al.
12,318,551 B2 6/2025 Jahangir
12,329,958 B2 6/2025 Siess et al.
12,337,163 B2 6/2025 Radman
12,343,516 B2 7/2025 Cook
12,343,518 B2 7/2025 Tuval et al.
12,343,519 B2 7/2025 Siess et al.
12,364,799 B2 7/2025 Siess et al.
12,364,850 B2 7/2025 Siess et al.
12,364,854 B2 7/2025 Wang
12,383,704 B2 8/2025 Ship et al.
12,383,724 B2 8/2025 Kirchoff et al.
12,383,727 B2 8/2025 Kassel et al.
12,390,633 B2 8/2025 Stotz et al.
12,397,146 B2 8/2025 Hart et al.
D1,092,716 S 9/2025 Bernazani
12,409,311 B2 9/2025 Jahangir et al.
12,415,056 B2 9/2025 Siess et al.
12,420,076 B2 9/2025 Spanier et al.
12,420,079 B2 9/2025 Das et al.
12,434,060 B2 10/2025 Tan et al.
12,440,663 B2 10/2025 Tuval et al.
12,440,665 B2 10/2025 Tuval et al.
12,447,309 B2 10/2025 Siess et al.
12,447,327 B2 10/2025 Stotz
12,453,847 B2 10/2025 Scheffler et al.
12,453,848 B2 10/2025 Tuval et al.
12,453,849 B2 10/2025 VanCamp et al.
D1,101,157 S 11/2025 Qi et al.
12,458,792 B2 11/2025 Zarins
12,465,744 B2 11/2025 Schuelke et al.
12,465,748 B2 11/2025 Calomeni et al.
12,478,774 B2 11/2025 Muller
12,478,775 B2 11/2025 Schlebusch et al.
12,478,776 B2 11/2025 Stotz
12,480,496 B2 11/2025 Mohl
12,491,062 B2 12/2025 Schwammenthal et al.
12,494,292 B2 12/2025 El Katerji et al.
12,502,521 B2 12/2025 Siess et al.
12,502,522 B1 12/2025 Van Horne et al.
12,515,036 B2 1/2026 Bette et al.
12,515,038 B2 1/2026 Weber et al.
12,521,546 B2 1/2026 Siess et al.
12,523,228 B2 1/2026 Schuelke et al.
12,539,413 B2 2/2026 Salahieh et al.
12,544,537 B2 2/2026 Siess et al.
12,544,553 B2 2/2026 Kapur et al.
12,544,554 B2 2/2026 Tuval et al.
12,544,558 B2 2/2026 Siess et al.
12,544,559 B2 2/2026 Barry
12,546,320 B2 2/2026 Siess et al.
12,551,677 B2 2/2026 Korkuch et al.
12,551,687 B2 2/2026 Grauwinkel et al.
12,558,526 B2 2/2026 Siess et al.
12,558,529 B2 2/2026 Zarins et al.
12,569,666 B2 3/2026 Siess et al.
12,569,669 B2 3/2026 Tuval et al.
12,575,841 B2 3/2026 Gao et al.
12,576,262 B2 3/2026 Edwards et al.
12,580,111 B1 3/2026 Mourran et al.
12,589,235 B2 3/2026 Spanier
12,589,237 B2 3/2026 Mitze et al.
12,589,238 B2 3/2026 Vollmer et al.
12,611,534 B2 4/2026 Haddadi et al.
2001/0009645 A1 7/2001 Noda
2001/0041934 A1 11/2001 Yamazaki et al.
2002/0031436 A1 3/2002 Maeda et al.
2002/0076322 A1 6/2002 Maeda et al.
2002/0082585 A1 6/2002 Carroll et al.
2002/0147495 A1 10/2002 Petroff
2002/0153664 A1 10/2002 Schroeder
2003/0060685 A1 3/2003 Houser
2003/0091450 A1 5/2003 Davis et al.
2003/0100816 A1 5/2003 Siess
2003/0111800 A1 6/2003 Kreutzer
2003/0139643 A1 7/2003 Smith et al.
2003/0191357 A1 10/2003 Frazier
2003/0199727 A1 10/2003 Burke
2004/0044266 A1 3/2004 Siess et al.
2004/0066107 A1 4/2004 Gery
2004/0102674 A1 5/2004 Zadini et al.
2004/0115038 A1 6/2004 Nuesser et al.
2004/0167376 A1 8/2004 Peters et al.
2004/0234391 A1 11/2004 Izraelev
2004/0241019 A1 12/2004 Goldowsky
2004/0260346 A1 12/2004 Overall et al.
2005/0006083 A1 1/2005 Chen et al.
2005/0008509 A1 1/2005 Chang
2005/0019167 A1 1/2005 Nusser et al.
2005/0085683 A1 4/2005 Bolling et al.
2005/0220636 A1 10/2005 Henein et al.
2005/0254976 A1 11/2005 Carrier et al.
2006/0030809 A1 2/2006 Barzilay et al.
2006/0062672 A1 3/2006 McBride et al.
2006/0155158 A1 7/2006 Aboul-Hosn
2006/0224110 A1 10/2006 Scott et al.
2006/0276682 A1 12/2006 Bolling et al.
2007/0004959 A1 1/2007 Carrier et al.
2007/0142696 A1 6/2007 Crosby et al.
2007/0156006 A1 7/2007 Smith et al.
2008/0015517 A1 1/2008 Geistert et al.
2008/0058925 A1 3/2008 Cohen
2008/0086027 A1 4/2008 Siess et al.
2008/0114339 A1 5/2008 McBride et al.
2008/0262289 A1 10/2008 Goldowsky
2008/0292478 A1 11/2008 Baykut et al.
2008/0306328 A1 12/2008 Ercolani
2009/0004037 A1 1/2009 Ito
2009/0112312 A1 4/2009 Larose et al.
2009/0138080 A1 5/2009 Siess et al.
2009/0203957 A1 8/2009 LaRose et al.
2009/0204205 A1 8/2009 Larose et al.
2010/0041939 A1 2/2010 Siess
2010/0082099 A1 4/2010 Vodermayer et al.
2010/0191035 A1 7/2010 Kang et al.
2010/0268017 A1 10/2010 Siess
2010/0298625 A1 11/2010 Reichenbach et al.
2011/0172505 A1 7/2011 Kim
2011/0184224 A1 7/2011 Garrigue
2011/0230821 A1 9/2011 Babic
2011/0237863 A1 9/2011 Ricci et al.
2011/0238172 A1 9/2011 Akdis
2012/0029265 A1 2/2012 LaRose
2012/0035645 A1 2/2012 Gross
2012/0088954 A1 4/2012 Foster

(56) References Cited

U.S. PATENT DOCUMENTS

| | | | |
|---|---|---|---|
| 2012/0093628 | A1 | 4/2012 | Liebing |
| 2012/0134793 | A1 | 5/2012 | Wu et al. |
| 2012/0172655 | A1 | 7/2012 | Campbell et al. |
| 2012/0178986 | A1 | 7/2012 | Campbell et al. |
| 2012/0245404 | A1 | 9/2012 | Smith |
| 2012/0247200 | A1 | 10/2012 | Ahonen et al. |
| 2012/0283506 | A1 | 11/2012 | Meister et al. |
| 2012/0310036 | A1 | 12/2012 | Peters et al. |
| 2013/0053623 | A1 | 2/2013 | Evans |
| 2013/0085318 | A1 | 4/2013 | Toellner |
| 2013/0209292 | A1 | 8/2013 | Baykut et al. |
| 2013/0281761 | A1 | 10/2013 | Kapur |
| 2013/0289376 | A1 | 10/2013 | Lang |
| 2013/0303830 | A1 | 11/2013 | Zeng et al. |
| 2013/0303831 | A1 | 11/2013 | Evans |
| 2013/0303832 | A1 | 11/2013 | Wampler |
| 2013/0330219 | A1 | 12/2013 | LaRose et al. |
| 2014/0005467 | A1 | 1/2014 | Farnan et al. |
| 2014/0030122 | A1 | 1/2014 | Ozaki |
| 2014/0051908 | A1 | 2/2014 | Khanal et al. |
| 2014/0079557 | A1 | 3/2014 | LaRose et al. |
| 2014/0107399 | A1 | 4/2014 | Spence |
| 2014/0128659 | A1 | 5/2014 | Heuring et al. |
| 2014/0167545 | A1 | 6/2014 | Bremner et al. |
| 2014/0194717 | A1 | 7/2014 | Wildhirt et al. |
| 2014/0200389 | A1 | 7/2014 | Yanai et al. |
| 2014/0207232 | A1 | 7/2014 | Garrigue |
| 2014/0275721 | A1 | 9/2014 | Yanai et al. |
| 2014/0330069 | A1 | 11/2014 | Hastings et al. |
| 2014/0341726 | A1 | 11/2014 | Wu et al. |
| 2014/0368942 | A1 | 12/2014 | Harrell |
| 2015/0031936 | A1 | 1/2015 | LaRose et al. |
| 2015/0051435 | A1 | 2/2015 | Siess et al. |
| 2015/0051438 | A1 | 2/2015 | Taskin |
| 2015/0080743 | A1 | 3/2015 | Siess |
| 2015/0099923 | A1 | 4/2015 | Magovern et al. |
| 2015/0141842 | A1 | 5/2015 | Spanier et al. |
| 2015/0171694 | A1 | 6/2015 | Dallas |
| 2015/0174307 | A1 | 6/2015 | Eckman et al. |
| 2015/0190092 | A1 | 7/2015 | Mori |
| 2015/0258262 | A1 | 9/2015 | Pfeffer |
| 2015/0273184 | A1 | 10/2015 | Scott et al. |
| 2015/0290372 | A1 | 10/2015 | Muller et al. |
| 2015/0290373 | A1 | 10/2015 | Rudser et al. |
| 2015/0306291 | A1 | 10/2015 | Bonde et al. |
| 2015/0343179 | A1 | 12/2015 | Schumacher et al. |
| 2015/0362017 | A1 | 12/2015 | Bell |
| 2015/0365738 | A1 | 12/2015 | Purvis et al. |
| 2016/0008531 | A1 | 1/2016 | Wang et al. |
| 2016/0030649 | A1 | 2/2016 | Zeng |
| 2016/0038663 | A1 | 2/2016 | Taskin et al. |
| 2016/0045654 | A1 | 2/2016 | Connor |
| 2016/0067395 | A1 | 3/2016 | Jimenez et al. |
| 2016/0101224 | A1 | 4/2016 | Akkerman |
| 2016/0126794 | A1 | 5/2016 | Gery |
| 2016/0144089 | A1 | 5/2016 | Woo et al. |
| 2016/0144166 | A1 | 5/2016 | Decréet al. |
| 2016/0166747 | A1 | 6/2016 | Frazier et al. |
| 2016/0184499 | A1 | 6/2016 | Ricci |
| 2016/0213828 | A1 | 7/2016 | Sievers |
| 2016/0223086 | A1 | 8/2016 | Balsells et al. |
| 2016/0256620 | A1 | 9/2016 | Scheckel et al. |
| 2016/0279311 | A1 | 9/2016 | Cecere et al. |
| 2016/0367739 | A1 | 12/2016 | Wiesener et al. |
| 2016/0375187 | A1 | 12/2016 | Lee et al. |
| 2017/0021069 | A1 | 1/2017 | Hodges |
| 2017/0021074 | A1 | 1/2017 | Opfermann et al. |
| 2017/0035952 | A1 | 2/2017 | Muller |
| 2017/0043074 | A1 | 2/2017 | Siess |
| 2017/0049947 | A1 | 2/2017 | Corbett et al. |
| 2017/0080136 | A1 | 3/2017 | Janeczek et al. |
| 2017/0087286 | A1 | 3/2017 | Spanier et al. |
| 2017/0087288 | A1 | 3/2017 | Groß-Hardt et al. |
| 2017/0128644 | A1 | 5/2017 | Foster |
| 2017/0136225 | A1 | 5/2017 | Siess et al. |
| 2017/0143952 | A1 | 5/2017 | Siess et al. |
| 2017/0157309 | A1 | 6/2017 | Begg et al. |
| 2017/0209633 | A1 | 7/2017 | Cohen |
| 2017/0232169 | A1 | 8/2017 | Muller |
| 2017/0274128 | A1 | 9/2017 | Tamburino et al. |
| 2017/0317573 | A1 | 11/2017 | Mueller et al. |
| 2017/0333607 | A1 | 11/2017 | Zarins |
| 2017/0333608 | A1 | 11/2017 | Zeng |
| 2017/0340787 | A1 | 11/2017 | Corbett et al. |
| 2017/0340788 | A1 | 11/2017 | Korakianitis et al. |
| 2017/0340789 | A1 | 11/2017 | Bonde et al. |
| 2017/0343043 | A1 | 11/2017 | Walsh et al. |
| 2018/0015214 | A1 | 1/2018 | Lynch |
| 2018/0021494 | A1 | 1/2018 | Muller et al. |
| 2018/0021495 | A1 | 1/2018 | Muller et al. |
| 2018/0050141 | A1 | 2/2018 | Corbett et al. |
| 2018/0055979 | A1 | 3/2018 | Corbett et al. |
| 2018/0064860 | A1 | 3/2018 | Nunez et al. |
| 2018/0093070 | A1 | 4/2018 | Cottone |
| 2018/0099076 | A1 | 4/2018 | LaRose |
| 2018/0110907 | A1 | 4/2018 | Keenan et al. |
| 2018/0133379 | A1 | 5/2018 | Farnan et al. |
| 2018/0154058 | A1 | 6/2018 | Menon et al. |
| 2018/0169312 | A1 | 6/2018 | Barry |
| 2018/0169313 | A1 | 6/2018 | Schwammenthal et al. |
| 2018/0207336 | A1 | 7/2018 | Solem |
| 2018/0212500 | A1 | 7/2018 | Bendixen |
| 2018/0219452 | A1 | 8/2018 | Boisclair |
| 2018/0221551 | A1 | 8/2018 | Tanner et al. |
| 2018/0221553 | A1 | 8/2018 | Taskin |
| 2018/0228950 | A1 | 8/2018 | Janeczek et al. |
| 2018/0228953 | A1 | 8/2018 | Siess et al. |
| 2018/0243004 | A1 | 8/2018 | von Segesser et al. |
| 2018/0243489 | A1 | 8/2018 | Haddadi |
| 2018/0250456 | A1 | 9/2018 | Nitzan et al. |
| 2018/0256797 | A1 | 9/2018 | Schenck et al. |
| 2018/0280598 | A1 | 10/2018 | Curran et al. |
| 2018/0289877 | A1 | 10/2018 | Schumacher et al. |
| 2018/0303990 | A1 | 10/2018 | Siess et al. |
| 2018/0303991 | A1 | 10/2018 | Nüsser et al. |
| 2018/0311421 | A1 | 11/2018 | Tuseth |
| 2018/0311423 | A1 | 11/2018 | Zeng et al. |
| 2018/0318483 | A1 | 11/2018 | Dague et al. |
| 2018/0318547 | A1 | 11/2018 | Yokoyama |
| 2018/0326132 | A1 | 11/2018 | Maimon et al. |
| 2018/0333059 | A1 | 11/2018 | Casas |
| 2018/0335037 | A1 | 11/2018 | Shambaugh et al. |
| 2018/0345028 | A1 | 12/2018 | Aboud et al. |
| 2018/0361042 | A1 | 12/2018 | Fitzgerald et al. |
| 2018/0369469 | A1 | 12/2018 | Le Duc De Lillers et al. |
| 2019/0001034 | A1 | 1/2019 | Taskin et al. |
| 2019/0004037 | A1 | 1/2019 | Zhang et al. |
| 2019/0030228 | A1 | 1/2019 | Keenan et al. |
| 2019/0046702 | A1 | 2/2019 | Siess et al. |
| 2019/0046703 | A1 | 2/2019 | Shambaugh et al. |
| 2019/0054223 | A1 | 2/2019 | Frazier et al. |
| 2019/0060539 | A1 | 2/2019 | Siess et al. |
| 2019/0060543 | A1 | 2/2019 | Khanal et al. |
| 2019/0076167 | A1 | 3/2019 | Fantuzzi et al. |
| 2019/0083690 | A1 | 3/2019 | Siess et al. |
| 2019/0099532 | A1 | 4/2019 | Er |
| 2019/0101130 | A1 | 4/2019 | Bredenbreuker et al. |
| 2019/0105437 | A1 | 4/2019 | Siess et al. |
| 2019/0117865 | A1 | 4/2019 | Walters et al. |
| 2019/0125948 | A1 | 5/2019 | Stanfield et al. |
| 2019/0143016 | A1 | 5/2019 | Corbett et al. |
| 2019/0143018 | A1 | 5/2019 | Salahieh et al. |
| 2019/0154053 | A1 | 5/2019 | McBride et al. |
| 2019/0167122 | A1 | 6/2019 | Obermiller et al. |
| 2019/0167875 | A1 | 6/2019 | Simon et al. |
| 2019/0167878 | A1 | 6/2019 | Rowe |
| 2019/0170153 | A1 | 6/2019 | Scheckel |
| 2019/0175806 | A1 | 6/2019 | Tuval et al. |
| 2019/0184078 | A1 | 6/2019 | Zilbershlag et al. |
| 2019/0184080 | A1 | 6/2019 | Mohl |
| 2019/0192752 | A1 | 6/2019 | Tiller et al. |
| 2019/0199165 | A1 | 6/2019 | Carson |
| 2019/0201603 | A1 | 7/2019 | Siess et al. |
| 2019/0209755 | A1 | 7/2019 | Nix et al. |

(56) References Cited

U.S. PATENT DOCUMENTS

2019/0209758 A1 7/2019 Tuval et al.
2019/0211836 A1 7/2019 Schumacher et al.
2019/0211846 A1 7/2019 Liebing
2019/0211847 A1 7/2019 Walsh et al.
2019/0223877 A1 7/2019 Nitzen et al.
2019/0269840 A1 9/2019 Tuval et al.
2019/0275224 A1 9/2019 Hanson et al.
2019/0282741 A1 9/2019 Franano et al.
2019/0282744 A1 9/2019 D'Ambrosio et al.
2019/0282746 A1 9/2019 Judisch
2019/0290817 A1 9/2019 Guo et al.
2019/0298902 A1 10/2019 Siess et al.
2019/0316591 A1 10/2019 Toellner
2019/0321527 A1 10/2019 King et al.
2019/0321529 A1 10/2019 Korakianitis et al.
2019/0321531 A1 10/2019 Cambronne et al.
2019/0336664 A1 11/2019 Liebing
2019/0344000 A1 11/2019 Kushwaha et al.
2019/0344001 A1 11/2019 Salahieh et al.
2019/0351117 A1 11/2019 Cambronne et al.
2019/0351119 A1 11/2019 Cambronne et al.
2019/0351120 A1 11/2019 Kushwaha et al.
2019/0358378 A1 11/2019 Schumacher
2019/0358379 A1 11/2019 Wiessler et al.
2019/0358384 A1 11/2019 Epple
2019/0365975 A1 12/2019 Muller et al.
2019/0383298 A1 12/2019 Toellner
2020/0016309 A1 1/2020 Kallenbach et al.
2020/0023109 A1 1/2020 Epple
2020/0030507 A1 1/2020 Higgins et al.
2020/0030509 A1 1/2020 Siess et al.
2020/0030510 A1 1/2020 Higgins
2020/0030511 A1 1/2020 Higgins
2020/0030512 A1 1/2020 Higgins et al.
2020/0038567 A1 2/2020 Siess et al.
2020/0038568 A1 2/2020 Higgins et al.
2020/0038571 A1 2/2020 Jahangir
2020/0069857 A1 3/2020 Schwammenthal et al.
2020/0088207 A1 3/2020 Schumacher et al.
2020/0114053 A1 4/2020 Salahieh et al.
2020/0129684 A1 4/2020 Pfeffer et al.
2020/0139028 A1 5/2020 Scheckel et al.
2020/0139029 A1 5/2020 Scheckel et al.
2020/0147283 A1 5/2020 Tanner et al.
2020/0164125 A1 5/2020 Muller et al.
2020/0164126 A1 5/2020 Muller
2020/0261633 A1 8/2020 Spanier
2020/0345337 A1 11/2020 Muller et al.
2020/0350812 A1 11/2020 Vogt et al.
2021/0052793 A1 2/2021 Struthers et al.
2021/0236803 A1 8/2021 Stotz
2021/0268264 A1 9/2021 Stotz
2021/0290929 A1 9/2021 Stotz
2021/0290930 A1 9/2021 Kasel
2021/0290932 A1 9/2021 Stotz
2021/0290937 A1 9/2021 Baumbach
2021/0313869 A1 10/2021 Strasswiemer et al.
2021/0316133 A1 10/2021 Kassel et al.
2021/0322756 A1 10/2021 Vollmer et al.
2021/0330958 A1 10/2021 Stotz et al.
2021/0338999 A1 11/2021 Stotz et al.
2021/0339004 A1 11/2021 Schlebusch et al.
2021/0339005 A1 11/2021 Stotz et al.
2021/0346678 A1 11/2021 Baumbach et al.
2021/0346680 A1 11/2021 Vogt et al.
2021/0379352 A1 12/2021 Schlebusch et al.
2021/0379355 A1 12/2021 Schuelke et al.
2021/0379358 A1 12/2021 Schuelke et al.
2021/0384812 A1 12/2021 Vollmer et al.
2022/0008714 A1 1/2022 Stotz
2022/0016411 A1 1/2022 Winterwerber
2022/0072296 A1 3/2022 Mori
2022/0072297 A1 3/2022 Tuval et al.
2022/0080178 A1 3/2022 Salahieh et al.
2022/0080180 A1 3/2022 Siess et al.
2022/0080182 A1 3/2022 Earles et al.
2022/0080183 A1 3/2022 Earles et al.
2022/0080184 A1 3/2022 Clifton et al.
2022/0080185 A1 3/2022 Clifton et al.
2022/0105337 A1 4/2022 Salahieh et al.
2022/0105339 A1 4/2022 Nix et al.
2022/0126083 A1 4/2022 Grauwinkel et al.
2022/0161018 A1 5/2022 Mitze et al.
2022/0161019 A1 5/2022 Mitze et al.
2022/0161021 A1 5/2022 Mitze et al.
2022/0241580 A1 8/2022 Stotz et al.
2022/0249829 A1 8/2022 Edwards et al.
2022/0323742 A1 10/2022 Grauwinkel et al.
2023/0001178 A1 1/2023 Corbett et al.
2023/0063798 A1 3/2023 Edwards et al.
2023/0079625 A1 3/2023 Theran et al.
2023/0105131 A1 4/2023 Kerkhoffs et al.
2023/0125439 A1 4/2023 Malone et al.
2023/0128328 A1 4/2023 Malone et al.
2023/0130285 A1 4/2023 Malone et al.
2023/0149691 A1 5/2023 VanCamp et al.
2023/0149692 A1 5/2023 Larsen et al.
2023/0158289 A1 5/2023 Breidall et al.
2023/0233834 A1 7/2023 Alexander et al.
2023/0277833 A1 9/2023 Sharma et al.
2023/0277836 A1 9/2023 Schellenberg et al.
2023/0293878 A1 9/2023 Christof et al.
2023/0364411 A1 11/2023 Bette
2023/0381492 A1 11/2023 Alexander et al.
2024/0075277 A1 3/2024 Schellenberg
2024/0102475 A1 3/2024 Schuelke et al.
2024/0198084 A1 6/2024 Stotz
2024/0245902 A1 7/2024 Schlebusch et al.
2024/0269459 A1 8/2024 Schellenberg et al.
2024/0285935 A1 8/2024 Popov et al.
2024/0335651 A1 10/2024 Mitze et al.
2024/0399135 A1 12/2024 Stotz et al.
2025/0032773 A1 1/2025 Baumbach et al.
2025/0121177 A1 4/2025 West
2025/0144397 A1 5/2025 Kassel et al.
2025/0161660 A1 5/2025 Baumbach et al.
2025/0170388 A1 5/2025 Kerkhoffs et al.
2025/0339669 A1 11/2025 Stotz et al.
2026/0048254 A1 2/2026 Scheffler et al.
2026/0069857 A1 3/2026 Kassel et al.
2026/0124441 A1 5/2026 Bette

FOREIGN PATENT DOCUMENTS

AU 2012261669 1/2013
AU 2013203301 5/2013
AU 2013273663 1/2014
BR PI0904483-3 7/2011
CA 2 026 692 4/1992
CA 2 026 693 4/1992
CA 2 292 432 5/1998
CA 2 664 835 2/2008
CA 2 796 357 10/2011
CA 2 947 984 11/2022
CN 1222862 A 7/1999
CN 1254598 A 5/2000
CN 1376523 A 10/2002
CN 2535055 Y 2/2003
CN 1118304 C 8/2003
CN 2616217 5/2004
CN 1202871 C 5/2005
CN 1833736 A 9/2006
CN 200977306 11/2007
CN 101112628 1/2008
CN 101128168 2/2008
CN 201150675 11/2008
CN 101677812 3/2010
CN 201437016 4/2010
CN 201618200 11/2010
CN 201658687 12/2010
CN 201710717 1/2011
CN 201894758 7/2011
CN 102475923 5/2012
CN 102545538 7/2012

(56) References Cited

FOREIGN PATENT DOCUMENTS

| | | |
|---|---|---|
| CN | 202314596 | 7/2012 |
| CN | 102743801 | 10/2012 |
| CN | 103143072 | 6/2013 |
| CN | 103845766 | 6/2014 |
| CN | 103861162 | 6/2014 |
| CN | 103915980 | 7/2014 |
| CN | 203809157 | 9/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107921187 | 4/2018 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| CN | 215841206 | 2/2022 |
| CN | 217828630 | 11/2022 |
| CN | 218922664 | 4/2023 |
| CN | 116077106 | 5/2023 |
| CN | 116365757 | 6/2023 |
| CN | 219250364 | 6/2023 |
| CN | 116785582 | 9/2023 |
| CN | 116531654 | 11/2023 |
| CN | 116440404 | 3/2024 |
| CN | 117018427 | 3/2024 |
| CN | 117482377 | 4/2024 |
| CN | 118320293 | 7/2024 |
| CN | 118320294 | 7/2024 |
| CN | 113769260 | 9/2024 |
| CN | 118142074 | 9/2024 |
| CN | 118681125 | 9/2024 |
| CN | 118899971 | 11/2024 |
| DE | 1 001 642 | 1/1957 |
| DE | 11 65 144 | 3/1964 |
| DE | 27 07 951 | 9/1977 |
| DE | 26 24 058 | 12/1977 |
| DE | 3 545 214 | 7/1986 |
| DE | 41 05 278 | 8/1992 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 103 45 694 | 4/2005 |
| DE | 697 31 709 | 4/2005 |
| DE | 101 55 011 | 11/2005 |
| DE | 601 19 592 | 9/2006 |
| DE | 11 2004 001 809 | 11/2006 |
| DE | 20 2005 020 288 | 6/2007 |
| DE | 10 2006 019 206 | 10/2007 |
| DE | 10 2006 036 948 | 2/2008 |
| DE | 10 2008 060 357 | 6/2010 |
| DE | 10 2009 039 658 | 3/2011 |
| DE | 20 2009 018 416 | 8/2011 |
| DE | 10 2010 041 995 | 4/2012 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 10 2015 216 050 | 2/2017 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2017 209 917 | 12/2018 |
| DE | 10 2017 212 193 | 1/2019 |
| DE | 10 2018 207 564 | 11/2019 |
| DE | 10 2018 207 578 | 11/2019 |
| DE | 10 2018 207 585 | 11/2019 |
| DE | 10 2018 207 591 | 11/2019 |
| DE | 10 2018 207 594 | 11/2019 |
| DE | 10 2018 207 611 | 11/2019 |
| DE | 10 2018 207 622 | 11/2019 |
| DE | 10 2018 208 536 | 12/2019 |
| DE | 10 2018 208 540 | 12/2019 |
| DE | 10 2018 208 541 | 12/2019 |
| DE | 10 2018 208 550 | 12/2019 |
| DE | 10 2018 208 945 | 12/2019 |
| DE | 10 2018 210 076 | 12/2019 |
| DE | 10 2018 207 624 | 1/2020 |
| DE | 10 2018 211 327 | 1/2020 |
| DE | 10 2018 211 328 | 1/2020 |
| DE | 10 2018 212 153 | 1/2020 |
| DE | 10 2018 213 350 | 2/2020 |
| DE | 10 2018 220 658 | 6/2020 |
| DE | 10 2020 102 473 | 8/2021 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 904 630 | 3/1999 |
| EP | 0 916 359 | 5/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 047 872 | 9/2010 |
| EP | 2 129 410 | 9/2011 |
| EP | 2 403 109 | 1/2012 |
| EP | 2 187 807 | 6/2012 |
| EP | 2 330 724 | 8/2012 |
| EP | 3 326 567 | 10/2014 |
| EP | 1 898 971 | 3/2015 |
| EP | 2 519 273 | 8/2015 |
| EP | 2 217 302 | 9/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 1 931 403 | 1/2017 |
| EP | 3 127 562 | 2/2017 |
| EP | 2 585 129 | 3/2017 |
| EP | 2 646 068 | 3/2017 |
| EP | 3 187 210 | 7/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |

(56) References Cited

FOREIGN PATENT DOCUMENTS

| | | |
|---|---|---|
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 131 599 | 2/2019 |
| EP | 3 456 367 | 3/2019 |
| EP | 3 119 451 | 6/2019 |
| EP | 3 536 360 | 9/2019 |
| EP | 3 542 835 | 9/2019 |
| EP | 3 542 836 | 9/2019 |
| EP | 3 062 877 | 12/2019 |
| EP | 3 189 862 | 2/2020 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 720 520 | 10/2020 |
| EP | 3 069 738 | 12/2020 |
| EP | 3 069 740 | 12/2020 |
| EP | 3 131 597 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 808 404 | 4/2021 |
| EP | 3 821 938 | 5/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 914 330 | 12/2021 |
| EP | 3 928 825 | 12/2021 |
| EP | 3 556 409 | 1/2022 |
| EP | 3 624 868 | 1/2022 |
| EP | 3 955 985 | 2/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 967 270 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 990 047 | 5/2022 |
| EP | 3 219 339 | 6/2022 |
| EP | 3 737 310 | 7/2022 |
| EP | 3 899 994 | 8/2022 |
| EP | 4 039 320 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 4 137 193 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 809 959 | 7/2023 |
| EP | 3 912 673 | 7/2023 |
| EP | 4 218 897 | 8/2023 |
| EP | 4 218 898 | 8/2023 |
| EP | 4 218 899 | 8/2023 |
| EP | 2 961 984 | 9/2023 |
| EP | 3 352 808 | 9/2023 |
| EP | 3 554 576 | 10/2023 |
| EP | 3 615 102 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 4 252 825 | 10/2023 |
| EP | 4 252 826 | 10/2023 |
| EP | 4 252 828 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 808 390 | 11/2023 |
| EP | 4 061 470 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |

(56) References Cited

FOREIGN PATENT DOCUMENTS

| | | | |
|---|---|---|---|
| EP | 4 115 919 | | 1/2024 |
| EP | 3 634 526 | | 2/2024 |
| EP | 3 768 342 | | 2/2024 |
| EP | 3 768 347 | | 2/2024 |
| EP | 3 769 799 | | 2/2024 |
| EP | 3 790 606 | | 2/2024 |
| EP | 3 930 780 | | 2/2024 |
| EP | 3 782 695 | | 3/2024 |
| EP | 3 854 448 | | 3/2024 |
| EP | 4 140 532 | | 5/2024 |
| EP | 3 693 038 | | 6/2024 |
| EP | 3 768 344 | | 7/2024 |
| EP | 3 970 765 | | 7/2024 |
| EP | 4 419 042 | | 8/2024 |
| EP | 3 854 444 | | 9/2024 |
| EP | 4 384 259 | | 9/2024 |
| EP | 4 429 750 | | 9/2024 |
| EP | 3 534 985 | | 10/2024 |
| EP | 3 793 674 | | 10/2024 |
| EP | 3 893 957 | | 10/2024 |
| EP | 3 914 334 | | 10/2024 |
| EP | 3 618 885 | | 11/2024 |
| EP | 4 034 221 | | 11/2024 |
| EP | 4 087 641 | | 11/2024 |
| EP | 4 039 289 | | 12/2024 |
| EP | 4 477 250 | | 12/2024 |
| EP | 4 084 856 | | 1/2025 |
| EP | 4 483 939 | | 1/2025 |
| EP | 4 483 940 | | 1/2025 |
| EP | 4 491 213 | | 1/2025 |
| EP | 3 522 947 | | 2/2025 |
| EP | 4 429 754 | | 2/2025 |
| EP | 3 998 102 | | 3/2025 |
| EP | 4 429 751 | | 3/2025 |
| EP | 4 429 752 | | 3/2025 |
| EP | 4 429 753 | | 3/2025 |
| EP | 4 023 282 | | 4/2025 |
| EP | 3 950 043 | | 5/2025 |
| EP | 3 955 986 | | 5/2025 |
| EP | 3 958 921 | | 5/2025 |
| EP | 4 218 900 | | 5/2025 |
| EP | 4 429 755 | | 5/2025 |
| EP | 2 830 675 | | 6/2025 |
| EP | 3 965 845 | | 6/2025 |
| EP | 4 039 319 | | 6/2025 |
| EP | 3 668 558 | | 7/2025 |
| EP | 3 780 041 | | 7/2025 |
| EP | 4 095 872 | | 7/2025 |
| EP | 3 668 559 | | 8/2025 |
| EP | 3 746 149 | | 8/2025 |
| EP | 3 823 687 | | 8/2025 |
| EP | 3 848 088 | | 8/2025 |
| EP | 4 119 184 | | 9/2025 |
| EP | 4 218 556 | | 9/2025 |
| EP | 4 046 678 | | 10/2025 |
| EP | 4 034 192 | | 12/2025 |
| EP | 4 100 106 | | 12/2025 |
| EP | 4 134 123 | | 1/2026 |
| EP | 4 201 467 | | 1/2026 |
| EP | 4 233 989 | | 1/2026 |
| EP | 3 650 076 | | 3/2026 |
| EP | 3 768 346 | | 3/2026 |
| EP | 4 034 184 | | 3/2026 |
| EP | 4 069 347 | | 3/2026 |
| EP | 4 090 412 | | 4/2026 |
| EP | 4 114 504 | | 4/2026 |
| EP | 3 852 833 | | 5/2026 |
| EP | 4 159 268 | | 5/2026 |
| EP | 4 223 356 | | 5/2026 |
| EP | 4 241 829 | | 5/2026 |
| EP | 4 279 119 | | 5/2026 |
| FR | 1458525 | | 3/1966 |
| FR | 2 768 056 | | 3/1999 |
| GB | 0 648 739 | | 1/1951 |
| GB | 2 213 541 | | 8/1989 |
| GB | 2 345 387 | | 7/2000 |
| GB | 2 451 161 | | 12/2011 |
| GB | 2 504 177 | | 1/2014 |
| GB | 2 545 062 | | 6/2017 |
| GB | 2 545 750 | | 6/2017 |
| JP | 59-119788 | | 8/1984 |
| JP | S61-500059 | | 1/1986 |
| JP | S62-113555 | | 7/1987 |
| JP | S64-68236 | | 3/1989 |
| JP | H02-055886 | | 2/1990 |
| JP | H02-079738 | | 3/1990 |
| JP | H04-176471 | | 6/1992 |
| JP | H04-108384 | | 9/1992 |
| JP | H08-057042 | | 3/1996 |
| JP | H08-504621 | | 5/1996 |
| JP | H10-052489 | | 2/1998 |
| JP | 2888609 | | 5/1999 |
| JP | 2889384 | | 5/1999 |
| JP | H11-239617 | | 9/1999 |
| JP | 2001-037728 | | 2/2001 |
| JP | 2001-515374 | | 9/2001 |
| JP | 2001-515375 | | 9/2001 |
| JP | 2003-019197 | | 1/2003 |
| JP | 2003-525438 | | 8/2003 |
| JP | 2003-528697 | | 9/2003 |
| JP | 2004-019468 | | 1/2004 |
| JP | 2004-515278 | | 5/2004 |
| JP | 2004-278375 | | 10/2004 |
| JP | 2005-028137 | | 2/2005 |
| JP | 2005-507039 | | 3/2005 |
| JP | 2007-222644 | | 9/2007 |
| JP | 2008-511414 | | 4/2008 |
| JP | 2008-516654 | | 5/2008 |
| JP | 2010-503495 | | 2/2010 |
| JP | 2010-518907 | | 6/2010 |
| JP | 2010-258181 | | 11/2010 |
| JP | 2010-534080 | | 11/2010 |
| JP | 2013-013216 | | 1/2013 |
| JP | 2013-519497 | | 5/2013 |
| JP | 2014-004303 | | 1/2014 |
| JP | 2014-524274 | | 9/2014 |
| JP | 2015-514529 | | 5/2015 |
| JP | 2015-514531 | | 5/2015 |
| JP | 2015-122448 | | 7/2015 |
| JP | 2016-002466 | | 1/2016 |
| JP | 2016-532500 | | 10/2016 |
| JP | 6063151 | | 1/2017 |
| JP | 6267625 | | 1/2018 |
| JP | 2018-057878 | | 4/2018 |
| JP | 2019-508128 | | 3/2019 |
| JP | 2019-516458 | | 6/2019 |
| JP | 6572056 | | 9/2019 |
| JP | 2020-072985 | | 5/2020 |
| JP | 2020-523090 | | 8/2020 |
| JP | 2018-510708 | | 3/2021 |
| JP | 2019-509141 | | 2/2022 |
| KR | 10-2011-0098192 | | 9/2011 |
| RO | 131676 | | 2/2017 |
| RU | 2 051 695 | | 1/1996 |
| TW | 374317 | | 11/1999 |
| UA | 97202 | C2 | 1/2012 |
| WO | WO 94/009835 | | 5/1994 |
| WO | WO 97/037696 | | 10/1997 |
| WO | WO 97/039785 | | 10/1997 |
| WO | WO 99/049912 | | 10/1999 |
| WO | WO 00/033446 | | 6/2000 |
| WO | WO 02/022200 | | 3/2002 |
| WO | WO 02/041935 | | 5/2002 |
| WO | WO 02/070039 | | 9/2002 |
| WO | WO 03/075981 | | 9/2003 |
| WO | WO 03/103745 | | 12/2003 |
| WO | WO 2005/020848 | | 3/2005 |
| WO | WO 2005/028014 | | 3/2005 |
| WO | WO 2005/037345 | | 4/2005 |
| WO | WO 2007/033933 | | 3/2007 |
| WO | WO 2007/105842 | | 9/2007 |
| WO | WO 2008/017289 | | 2/2008 |
| WO | WO 2008/081783 | | 7/2008 |
| WO | WO 2009/010888 | | 1/2009 |

(56) References Cited

FOREIGN PATENT DOCUMENTS

| | | |
|---|---|---|
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2014/042925 | 3/2014 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/007120 | 1/2018 |
| WO | WO 2018/036927 | 3/2018 |
| WO | WO 2018/039479 | 3/2018 |
| WO | WO 2018/088939 | 3/2018 |
| WO | WO 2018/081040 | 5/2018 |
| WO | WO 2018/089970 | 5/2018 |
| WO | WO 2018/109038 | 6/2018 |
| WO | WO 2018/139508 | 8/2018 |
| WO | WO 2018/146045 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/067233 | 4/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/191245 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/176236 | 9/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2020/245649 | 12/2020 |
| WO | WO 2020/264174 | 12/2020 |
| WO | WO 2021/046275 | 3/2021 |
| WO | WO 2021/062265 | 4/2021 |
| WO | WO 2021/067169 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2021/191106 | 9/2021 |
| WO | WO 2023/040546 | 12/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/173977 | 8/2022 |
| WO | WO 2022/174249 | 8/2022 |
| WO | WO 2023/226779 | 9/2022 |
| WO | WO 2023/278599 | 1/2023 |
| WO | WO 2023/014742 | 2/2023 |
| WO | WO 2023/037162 | 3/2023 |
| WO | WO 2023/049813 | 3/2023 |
| WO | WO 2024/160098 | 4/2023 |
| WO | WO 2023/076461 | 5/2023 |
| WO | WO 2023/076869 | 5/2023 |
| WO | WO 2023/230157 | 11/2023 |
| WO | WO 2024/104184 | 5/2024 |
| WO | WO 2024/243154 | 11/2024 |
| WO | WO 2025/226734 | 10/2025 |
| WO | WO 2026/072583 | 4/2026 |

OTHER PUBLICATIONS

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

International Search Report and Written Opinion received in PCT Application No. PCT/EP2019/062746, dated Aug. 16, 2019 in 11 pages.

International Preliminary Report on Patentability and Written Opinion received in PCT Application No. PCT/EP2019/062746, dated Nov. 26, 2020 in 8 pages.

(56) References Cited

OTHER PUBLICATIONS

Delgado et al., "Interventional Treatment of Advanced Ischemic Heart Disease", Percutaneous Mechanical Assist Devices, Ch. 6, Springer, 2009, pp. 85-91.
Delgado et al., "Interventional Treatment of Advanced Ischemic Heart Disease", The Future of Treatment of Advanced Ischemic Heart Disease, Ch. 8, Springer, 2009, pp. 129-142.
Eeckhout, MD, PhD, et al., "Handbook of Complications During Percutaneous Cardiovascular Interventions", 2007 Informa UK Ltd., Ch. 12, pp. 167-177.
"FDA Approves Abiomed's Heart Pump Impella, Shares Rise", Reuters 2008 press release, Jun. 2, 2008, https://jp.reuters.com/article/us-abiomed/fda-approves-abiomeds-heart-pump-impella-shares-rise-idUSBNG131420080602/, 1 page.
Lake et al., "Pediatric Cardiac Anesthesia", 4th Edition, 2005, Ch. 15, pp. 291-303.
Machiraju, Venkat R., "Redo Cardiac Surgery in Adults", Practical Approaches to the Current "On- Pump" Redo Coronary Artery Bypass Surgery, Ch. 2, Springer, 2012, pp. 7-19.
Machiraju, Venkat R., "Redo Cardiac Surgery in Adults", Options for Advanced Mechanical Support for Cardiogenic Shock Complicating Cardiac Reoperations, Ch. 9, Springer, 2012, pp. 67-80.
Machiraju, Venkat R., "Redo Cardiac Surgery in Adults", Percutaneous Approaches to Valvular Heart Disease After Previous Cardiac Surgery, Ch. 21, Springer, 2012, pp. 195-200.
New Hampshire Ball Bearings, Inc., "Engineering Reference, Rod End & Spherical Bearings", https://www.nhbb.com/index.php/knowledge-center/engineering-reference/rod-end-spherical-bearings/self-lubricating-liner-systems, 2021, pp. 13.
Parrillo et al., "Critical Care Medicine", Principles of Diagnosis and Management in the Adult, Elsevier, 4th Edition, 2014, Chapters 4 & 29, pp. 47-58.e1 and 442-469.e4.
Schmitz-Rode, T, Graf, J, Pfeffer, J. et al. "An Expandable Percutaneous Catheter Pump for Left Ventricular Support: Proof of Concept", JACC. Jun. 2005, 45 (11) 1856-1861.
Vincent, MD, Phd, et al., "Textbook of Critical Care", Acute Coronary Syndromes: Therapy, Elsevier, 7th Edition, Ch. 78, 2017, pp. 520-531.e3.
Vincent, MD, PhD, et al., "Textbook of Critical Care", Mechanical Support in Cardiogenic Shock, Elsevier, 7th Edition, Ch. 91, 2017, pp. 637-648.e3.
Ai, X. (2013). Radial Bearings. In: Wang, Q.J., Chung, YW. (eds) Encyclopedia of Tribology. Springer, Boston, MA https://doi.org/10.1007/978-0-387-92897-5_334, accessed Oct. 18, 2024, pp. 4.
"Edwards SAPIEN 3 Kit—Transapical and Transaortic", Edwards Lifesciences, Released Nov. 8, 2016, p. 11. chrome-extension://efaidnbmnnnibpcajpcglclefindmkaj/https://edwardsprod.blob.core.windows.net/media/De/sapien3/doc-0045537b%20-%20certitude.pdf.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
GGB by Timken Bearings FAQ; "What is a Slide Bearing?;" https://www.ggbearings.com/en/why-choose-ggb/faq/bearings-faq/what-slide-bearing; accessed Oct. 10, 2024, pp. 1.
Google.com, "Spider Bearing—Search Results;" https://www.google.com/search?q=spider+bearing&rlz=X1C1GCEA_enUS1059US1059&oq=spider+beari&gs_lcrp=EgZjaHJvbWUqCQgAEEUYOxiABDIJCAAQRRg7GIAEMgYIARBFGDkyBwgCEAAYgAQyBwgDEAAYgAQyBwgEEAAYgAQyBwgFEAAYgAQyBwgGEAAYgAQyBggHEEUYPKgCALACAA&sourceid=chrome&ie=UTF-8, accessed Oct. 18, 2024, pp. 4.
Gopinath, Divya, "A System for Impedance Characterization of Coronary Stents", University of Strathclyde Engineering, Thesis, Aug. 2015, pp. 77.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
McMaster-Carr Online Catalog, "Bearings search results;" https://www.mcmaster.com/products/bearings/; accessed Oct. 18, 2024, pp. 5.
McMaster-Carr Online Catalog, "Slide Bearings search results;" https://www.mcmaster.com/products/slide-bearings/; accessed Oct. 18, 2024, pp. 21.
Neale, Michael J., "The Tribology Handbook;" 1999, Butterworth-Heinemann, Second Edition, pp. 582.
Park et al., "A Novel Electrical Potential Sensing Method for in Vitro Stent Fracture Monitoring and Detection", Jan. 1, 2011, vol. 21, No. 4, pp. 213-222.
RBCbearings.com, "RBC Bearings Incorporated—Products;" https://www.rbcbearings.com/Products; accessed Oct. 18, 2024, pp. 2.
Sak et al., "Influence of polyetheretherketone coatings on the Ti—13Nb—13Zr titanium alloy's bio-tribological properties and corrosion resistance;" Materials Science and Engineering: C, vol. 63, 2016, pp. 52-61.
SKF.com; "Products: Bearings;" https://www.skf.com/us/products/bearings; accessed Oct. 18, 2024, pp. 8.
Wikipedia, "Plain Bearing," https://en.wikipedia.org/wiki/Plain_bearing; accessed Oct. 18, 2024, pp. 10.

ROTOR BEARING SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 17/054,884, entitled ROTOR BEARING SYSTEM, and filed Jul. 13, 2021, which is the U.S. National Phase of international application number PCT/EP2019/062746, entitled ROTOR BEARING SYSTEM, and filed May 16, 2019, which claims the benefit of priority to German patent application number 102018207611.1, entitled ROTOR BEARING SYSTEM, and filed May 16, 2018, the disclosure of which is hereby incorporated by reference herein in its entirety for all purposes and forms a part of this specification.

BACKGROUND

Field

The present invention relates to a rotor bearing system.

Description of the Related Art

A combination of a solid-body bearing and a passive magnetic axial coupling is known in the state of the art. A radial passive magnetic coupling for torque transmission, which has an axial offset of a coupling part, i.e. a preload, for adjusting the axial force, is known as well.

The use of an axial passive magnetic coupling leads to a high axial force on the bearing arrangement, and consequently to increased friction and increased wear. The axial force to be received by the bearing cannot be minimized, because said force is a direct function of the torque to be transmitted.

Further known is also an arrangement having two fixed bearings for axial and radial support of the rotor in pumps, in particular in pumps for cardiovascular support (VAD). In the case of preloaded bearings, the use of two solid-body bearings represents an overdetermined bearing arrangement in which the preload is reduced by wear of the loaded bearing or bearings until there is a small amount of play and the bearing arrangement becomes underdetermined, which is disadvantageous. A thermally induced elongation or expansion of the rotor can furthermore not be compensated, so that the rotor may jam between the two axial bearings.

SUMMARY

The object of the invention is to provide a rotor bearing system in which less friction and therefore less wear occurs.

This object is achieved by the rotor bearing system specified in claim 1. Advantageous embodiments of the invention are specified in the dependent claims.

A rotor bearing system according to the invention is in particular used for the contactless transmission of a torque to a rotating rotor in combination with the support thereof in axial and radial direction.

A rotor bearing system according to the invention comprises a housing, in which a first in particular cylindrical permanent magnet is mounted such that it can rotate about a first axis.

A rotor bearing system according to the invention further comprises a rotor comprising a second hollow-cylindrical permanent magnet, which is mounted such that it can rotate about a second axis. The rotor preferably comprises a hollow-cylindrical part in which the second hollow-cylindrical permanent magnet is disposed.

In a rotor bearing system according to the invention, the first permanent magnet and the second permanent magnet overlap axially at least partially, wherein the first permanent magnet is disposed offset, in particular axially, relative to the second permanent magnet.

The phrase “the first permanent magnet is disposed axially offset relative to the second permanent magnet” means that an axial center of the first permanent magnet is disposed axially offset relative to an axial center of the second permanent magnet.

The axial center of a permanent magnet is hereby calculated as the point between the one axial end of the permanent magnet and the opposite other axial end of the permanent magnet. One axial end is located on an axial longitudinal axis of the permanent magnet.

The housing between the two permanent magnets is furthermore located in the axial overlap region of the first permanent magnet and the second permanent magnet.

The rotor bearing system also comprises a first bearing for the relative axial positioning of the rotor and the housing with respect to one another and for receiving an axial force resulting from the arrangement of the first permanent magnet and the second permanent magnet.

The rotor bearing system further comprises a second bearing and a third bearing for receiving radial forces and for positioning the axis of rotation of the second permanent magnet.

The axial offset of the first and the second permanent magnet relative to one another produces a force in axial direction between these bodies which, depending on the type of magnetization, acts in or preferably counter to the offset direction. This in particular makes it possible to set a positive, negative or disappearing axial force resulting from the coupling and other operating forces, e.g. from flow forces, in a defined manner, without simultaneously significantly reducing the transmittable torque. For this purpose, the axial force exerted on the rotor from the flow can be determined first, e.g. by evaluating flow simulations. The relationship between axial offset and magnetic axial force can be determined from magnetic simulations and/or measurements. An offset can then be selected for the design, in which the magnetic axial force at least compensates the flow axial force, preferably overcompensates the flow axial force by a safety factor.

In combination with the first bearing, i.e. an axial bearing, a defined axial force required for the bearing function can thus be set via the relative axial offset. Said axial force can be selected such that the first bearing can be operated within the allowable range with regard to friction and wear. It is preferred that the axial bearing is operated in constant contact, i.e. the magnetic axial force must at least compensate the flow axial force at all times.

In contrast to a solution realized in the state of the art with two axial solid-body bearings having the above-described disadvantages, the solution described here comprises only one axial solid-body bearing and thus avoids overdetermination or underdetermination. The specifically adjustable axial force from the magnetic coupling also ensures that the axial support by the solid-body bearing is sufficient in only one direction.

According to a preferred embodiment, the first permanent magnet and the second permanent magnet are arranged coaxially. This advantageously enables efficient coupling of the first and second permanent magnet.

It is further preferred that an axis of rotation of the rotor and an axis of the second permanent magnet are coaxial. This advantageously ensures that the rotor and the second permanent magnet are disposed in a symmetrical manner, which also facilitates the production of the rotor.

It is further preferred that an axis of rotation of the shaft and an axis of the first permanent magnet are coaxial. This advantageously ensures that the shaft and the first permanent magnet are easy to produce.

It is further preferred that an axis of rotation of the shaft and an axis of rotation of the rotor are coaxial. This advantageously ensures that the coupling between the first and the permanent magnet is efficient.

According to a preferred embodiment, the rotor comprises a conical or tapered part, which adjoins the hollow-cylindrical part. It is preferred here that the axis of the cone and the axis of rotation of the rotor, which is preferably coaxial with the axis of the second permanent magnet, are coaxial. The base of the conical part adjoins the hollow-cylindrical part in the direction of the bearing mounted between the rotor and the housing. The outer circumference of the base of the cone is hereby connected to the annular opening at an axial end of the hollow-cylindrical part.

According to another preferred embodiment, the second bearing is mounted on the end of the rotor facing away from the housing, i.e. on the end of the conical part facing away from the housing. It is preferred that the bearing is mounted between the rotor and an affixed component, whereby the affixed component is preferably permanently connected to the housing.

According to another preferred embodiment, the rotor comprises blades on the outer periphery of the rotor, preferably on the conical part of the rotor, which, when the rotor rotates, transports a liquid from the end of the rotor facing away from the housing toward the housing. It is preferred that the rotor comprises holes, so that the liquid is drawn from outside the rotor into a gap formed by the inner side of the hollow-cylindrical part of the rotor and an outer side of the housing, to then flow from the inside of the hollow-cylindrical part of the rotor flow through the conical part of the rotor to the end of the rotor facing away from the housing.

According to a preferred embodiment, the first bearing and the third bearing together form a combined axial and radial bearing which serves to receive axial and radial forces. The combined axial and radial bearing preferably comprises an axial bearing and a radial bearing.

According to a preferred embodiment, the first bearing and the third bearing are disposed between the housing and the rotor and the second bearing is disposed on the rotor. The first and third bearing are preferably a combined axial and radial bearing. The axial offset of the first and second permanent magnet is hereby set such that the housing is pressed in the direction of the rotor and/or the rotor is pressed in the direction of the housing.

According to a preferred embodiment, the combined axial and radial bearing is a solid-body bearing, which, in the rotor, preferably comprises a ball which rotates in a cone provided on the housing, thus allowing both radial and axial forces to be received. The material of the ball and/or the cone preferably comprises or consists of monocrystalline corundum or sapphire. These materials are ideal because of their high wear resistance.

According to a preferred embodiment, the first bearing and the third bearing are disposed on the rotor and the second bearing is disposed between the housing and the rotor.

The first and third bearing are preferably mounted on an end of the rotor facing away from the housing. The first and third bearing are mounted between the end of the rotor facing away from the housing and an affixed component, whereby the affixed component is preferably permanently connected to the housing.

The first and third bearing preferably form a combined axial and radial bearing. According to a preferred embodiment, the combined axial and radial bearing is a solid-body bearing, which preferably comprises a ball disposed in the rotor, which rotates in a cone attached to the affixed component, by means of which both radial and axial forces can be received. The material of the ball and/or the cone preferably comprises or consists of monocrystalline corundum or sapphire.

According to a preferred embodiment, the first and the third bearing are realized by two different structural elements. For example, the axial bearing function can be realized by the contact of a ball or other preferably convex surface disposed in the rotor with a preferably flat plate mounted on the housing. The radial bearing function can, for example, be realized by a hydrodynamic sliding bearing on the periphery of the rotor, preferably on the hollow-cylindrical part of the rotor at the level of the second permanent magnet.

The second or third bearing is preferably a hydrodynamic sliding bearing. The second or third bearing is preferably disposed on the periphery of the rotor.

According to a preferred embodiment, the housing is a motor housing which, in its interior, comprises a rotatably mounted shaft and the first permanent magnet disposed on said shaft. It is further preferred that a motor which drives the shaft is disposed in the motor housing. It is further preferred that the motor is completely sealed off from the environment by the motor housing, so that liquid cannot enter the motor housing and the motor, and substances from the interior of the motor also cannot leak into the surrounding liquid.

According to a preferred embodiment, both the first permanent magnet and the second permanent magnet respectively comprise at least one pole pair. The first permanent magnet preferably comprises the same number of pole pairs as the second permanent magnet. It is further preferred that the number of pole pairs is greater than two. This can advantageously ensure that the transmittable torque can be increased.

According to a preferred embodiment, the axial force originating from the coupling, i.e. a magnetic force, which results from the offset of the first and second permanent magnet and acts on the rotor, is selected to be greater than the hydraulic force. In this case, the hydraulic force is a reaction force which acts on the rotor and counteracts the direction of flow. This feature advantageously ensures that, at the first bearing, the rotor is pressed in the direction of the housing, so that the rotor and the housing do not lose contact at the first bearing. The magnetic axial force preferably overcompensates the flow axial force by a safety factor.

According to another preferred embodiment, the axial force originating from the coupling is selected to be smaller than the hydraulic force. The first bearing is only in contact when the system is at a standstill. This means that the hydraulic force on the rotor is at the nominal operating point.

In this case, the axial position during operation is entirely determined by the balance between the magnetic force and the hydraulic force.

According to a preferred embodiment, both the first permanent magnet and the second permanent magnet respectively comprise at least two axial segments.

By partitioning the radial coupling, which is realized by the first and second permanent magnet, into two or more segments in axial direction with a simultaneous axial offset of the segments relative to one another, the axial force can advantageously be increased. With comparable dimensions, overall length and outer diameter, the transmittable torque decreases, which can, however, be compensated by an axial elongation of the radial coupling or an increase in the number of pole pairs. Thus, both the torque and the axial force can be adjusted via the number of pole pairs, the exterior dimensions and the partitioning with distances between the segments. The number of segments and the distance between the segments determines the amount of axial force.

This measure can be taken, for example, if the magnetic axial force is insufficient to reliably compensate the flow force.

The number of segments of the first permanent magnet is preferably exactly the same as the number of segments of the second permanent magnet. This simplifies production and increases the symmetry of the device.

The first permanent magnet preferably has the same overall axial length as the second permanent magnet. The overall axial length is the sum of all segments and all spacers. It is hereby assumed that there is no gap between a segment and a spacer or another segment.

According to a preferred embodiment, one spacer is respectively disposed between adjacent segments of the first permanent magnet and/or the second permanent magnet. This can advantageously ensure that the two adjacent segments of a permanent magnet are spaced apart from one another by a predetermined axial distance. This also makes it possible to realize an axial preload, for example in order to be able to produce a defined axial force for a bearing function.

According to a preferred embodiment, at least one spacer comprises or consists of plastic, aluminum, titanium or another non-magnetic material. This has the advantage that the material of the spacer has little or no influence on the magnetic field, since said material is non-ferromagnetic.

According to a preferred embodiment, the second permanent magnet comprises a device for magnetic return. This device is preferably disposed on the outer side of the second permanent magnet. In addition to advantages in terms of production technology, this has the advantage that the torque of the coupling is increased, because fewer stray fields are lost.

According to a preferred embodiment, the first permanent magnet and/or the second permanent magnet has a radial, parallel or diametrical magnetization. These are common types of magnetization, which the person skilled in the art can adapt to the given circumstances of each individual case.

According to a preferred embodiment, the first permanent magnet and/or the second permanent magnet comprises a permanent magnet which comprises or is a Halbach array, i.e. which in particular has the magnet configuration of a Halbach array.

In the present case, a permanent magnet having the magnet configuration of a Halbach array is a permanent magnet in which the magnetic flux density is low on one side, the so-called weak side, because the magnetic flux is essentially canceled there, and high on another side, the so-called strong side, because the magnetic flux is amplified there.

In the present case, a Halbach array is an arrangement of magnets as they are described at the link https://en.wikipedia.org/wiki/Halbach_array, to which reference is hereby made and the disclosure of which is fully incorporated into the description of this invention.

The magnet configuration of a Halbach array can be formed by permanent-magnetic segments which are assembled and the magnetization direction of which relative to one another is tilted 90° with respect to a preferred direction, e.g. with respect to the direction of a longitudinal axis of the arrangement. It is thus possible to achieve a side-dependent flux amplification. For further information, please also refer to the relevant technical literature concerning Halbach arrays.

The first permanent magnet and/or the second permanent magnet is or are preferably a permanent magnet which comprises or is a Halbach array. This feature advantageously ensures that the magnetic flux can be concentrated on one side of the Halbach array (strong side). This is particularly advantageous in the case of the second permanent magnet, which is disposed on the outside, whereby the strong side of the Halbach array of the second breakdown magnet [sic] is directed toward the first permanent magnet.

The first permanent magnet and the second permanent magnet are magnetized such that a rotation of the first permanent magnet sets the second permanent magnet in rotation and vice versa. This characteristic is necessary to be able to transmit torque from the one permanent magnet to the other permanent magnet without contact.

Preferably, the first permanent magnet and the second permanent magnet together form a magnetic coupling which, due to the preferably radially directed magnetic field lines, is preferably a radial magnetic coupling.

According to a preferred embodiment, an axial force of the rotor bearing system can be freely adjusted by varying at least one of the following list. The list includes: a pole pair number of the first permanent magnet and the second permanent magnet; the dimensions of the segments of the first permanent magnet; the dimensions of the segments of the second permanent magnet; distances between adjacent segments of the first permanent magnet and the second permanent magnet;

distances between adjacent segments of the magnetic return; axial lengths of spacers between segments of the first permanent magnet and the second permanent magnet and segments of the magnetic return; a magnetization of the first permanent magnet; a magnetization of the second permanent magnet; a flow force which acts on the rotor during proper use; and an offset of the first permanent magnet relative to the second permanent magnet.

The person skilled in the art knows that the variables mentioned in the list influence the axial force. By varying at least one of the values in the list, preferably several values in the list, the axial force can be freely adjusted within predetermined limits. This can advantageously ensure that the axial force can appropriately be adapted to the given circumstances of each individual case.

The rotor preferably comprises at least one bore or at least one hole, preferably bores or holes. This advantageously ensures that the liquid transported by the rotor can flow into a space or gap between the rotor and the housing. This enables heat, produced for example by friction or by eddy currents in a possibly metal housing, to be dissipated. Furthermore, the continuous flow of the medium ideally prevents deposits of solid particles of the medium in the region of the gap and the bearing.

BRIEF DESCRIPTION OF THE DRAWINGS

Advantageous design examples of the invention are shown in the drawings and are explained in more detail in the following description.

DETAILED DESCRIPTION

Figure 1:
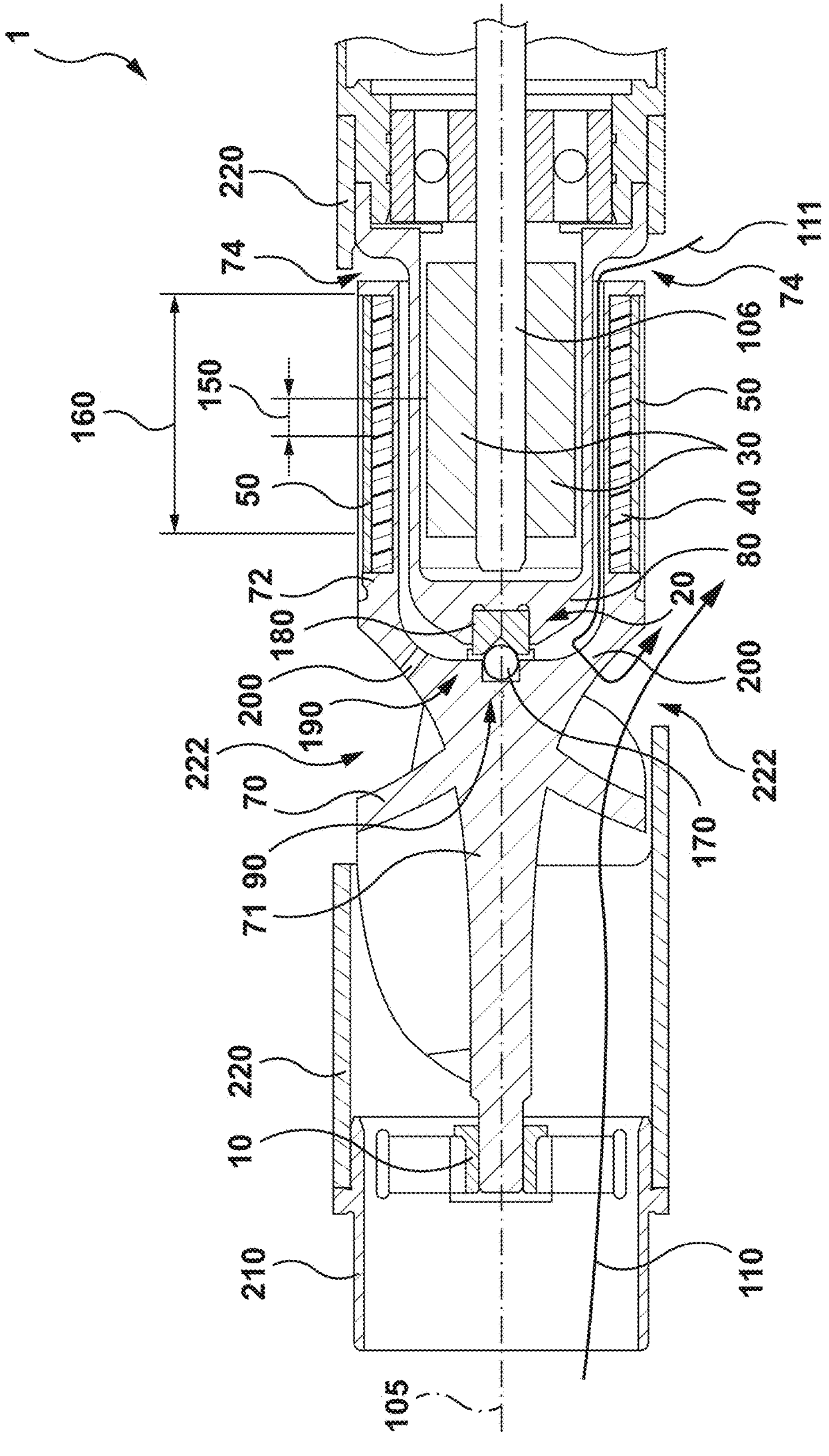
FIG. 1 shows a rotor bearing system according to an embodiment of the invention.

FIG. 1 shows a rotor bearing system 1 with contactless torque transmission and a radial and axial bearing of a rotor, which is designed in the form of a pump for cardiovascular support (VAD), for example.

The rotor bearing system 1 comprises a housing 80, here a motor housing, in which a first cylindrical permanent magnet 30 is seated and mounted on a shaft 106 driven by a not depicted motor such that it can rotate about a first axis 105. The housing 80 has an outer diameter of 3.5 mm.

The rotor bearing system 1 further comprises a rotor 70 for conveying a liquid, wherein the rotor 70 comprises a second hollow-cylindrical permanent magnet 40, which is likewise mounted such that it can rotate about the first axis 105. The second hollow-cylindrical permanent magnet 40 is mounted in a hollow-cylindrical part 72 of the rotor 70.

The second hollow-cylindrical permanent magnet 40 comprises a magnetic return 50 on its outer side.

The first permanent magnet 30 has an outer diameter of 3 mm, a magnet height of 1 mm and a length of 5 mm. The second permanent magnet 40 has an outer diameter of 5 mm, a magnet height of 0.5 mm and a length of 5 mm. The rotor 70 has an outer diameter of 5.3 mm and a length of 15 mm.

The rotor 70 is designed as an impeller, which converts the mechanical power transmitted by the coupling into hydraulic power for supporting a blood flow against a blood pressure.

The rotor 70 further comprises a conical or tapered part 71, which adjoins the hollow-cylindrical part 72. The outer circumference of the base of the conical part 71 is connected to the annular opening at an axial end of the hollow-cylindrical part 72.

The first permanent magnet 30 and the second permanent magnet 40 overlap axially at least partially in the axial region identified with the reference sign 160.

The first permanent magnet 30 is hereby disposed axially offset relative to the second permanent magnet 40. The centers of the first permanent magnet 30 and the second permanent magnet 40 are marked by vertical lines and the axial offset 150 is drawn in between these two dashed lines.

As a result of the axial offset 150, the second permanent magnet 40 experiences a force which, in FIG. 1, is directed toward the right, so that a ball 170 disposed in the rotor 70 is pressed onto a cone 180 mounted in the housing 80, so that a first bearing 20 and a third bearing 90, which here form a combined axial and radial bearing 190, is kept in contact. During proper use, the ball 170 rotates in the cone 180, as a result of which both radial and axial forces can be received.

The combined axial and radial bearing 190 here is a solid-body bearing. The ball 170 is disposed in the conical part 71. The axial and radial bearing function is achieved by combining the two elements ball 170 and cone 180.

The ball 170 has a diameter of 0.5 mm. The cone 180 has a diameter of 1 mm, a height of 0.8 mm and a cone angle of 90°.

The axial bearing function of the combined bearing 190 functions as the first bearing and is used for the relative axial positioning of the rotor 70 and the housing 80 or the shaft 106 relative to one another, and also for receiving an axial force resulting from the arrangement of the first permanent magnet 30 and the second permanent magnet 40.

The axial force in the rotor bearing system 1 can furthermore be freely adjusted, as a result of which the acting forces can be optimally adjusted.

In the overlap region 160 and in the region between the overlap region 160 and the rotor 70, the housing 80, which comprises the first permanent magnet 30, is surrounded by the rotor 70, in particular by the interior of the hollow-cylindrical part 72 of the rotor 70. A hollow-cylindrical channel 74 through which the liquid can flow is thus formed between the housing 80 and the rotor 70. In order to allow liquid to flow continuously from outside the conical part 71 of the rotor 70 into the channel 74, bores 200 are drilled into the rotor 70, preferably in the conical part 71 of the rotor 70, or at a transition from the conical part 71 to the hollow-cylindrical part 72 of the rotor 70. The flow direction of the liquid is indicated by arrow 110. Arrow 111 indicates a direction of flow of liquid through the channel 74.

A second bearing 10, which is designed as a radial, hydrodynamic and blood-lubricated sliding bearing, is mounted on the end of the conical part 71 of the rotor 70 facing away from the housing 80. The second bearing 10 is used to receive radial forces and to position the axis of rotation of the second permanent magnet 40, which is disposed in the rotor 70. The second bearing 10 is disposed between the rotor 70 and an insert 210 which is mounted, in particular clamped or press-fitted, on a second housing 220 in an annular end, which is in turn mounted on the housing 80. The second housing 220 forms an outer skin of the rotor bearing system 1, whereby numerous outlet windows 222 are present in the second housing 220, which can also be referred to as an impeller housing. The insert 210 is preferably a spider bearing that can be glued, welded or press-fitted into the second housing 220. The spider bearing 210 has an outer diameter of 6 mm and a length of 3 mm. The second housing 220 has an outer diameter of 6 mm, a length of 18 mm and a wall thickness of 0.25 mm.

The bearing 10 has a diameter of 1 mm and a length of 1 mm.

As a result of the axial offset 150 between the first permanent magnet 30 and the second permanent magnet 40 established by the design, in the design example of FIG. 1 a defined axial force acts on the rotor 70 in the direction of the motor; i.e. from left to right in the design example of FIG. 1. This force is counteracted by a hydraulic force on the rotor 70, i.e. from right to left in the design example of FIG. 1. In the present case, the axial force originating from the coupling of the first permanent magnet 30 and the second permanent magnet 40 is selected to be slightly greater than the hydraulic force. On the one hand, this ensures that the rotor 70 is always in a defined axial position and, on the other hand, that the combined axial and radial bearing 190 is not unnecessarily loaded. Consequently, friction and wear are kept low. To optimize the friction and wear behavior, the cone angle of the cone 180 can also be increased, whereby a sufficient radial load-bearing capacity has to be ensured.

Figure 2:
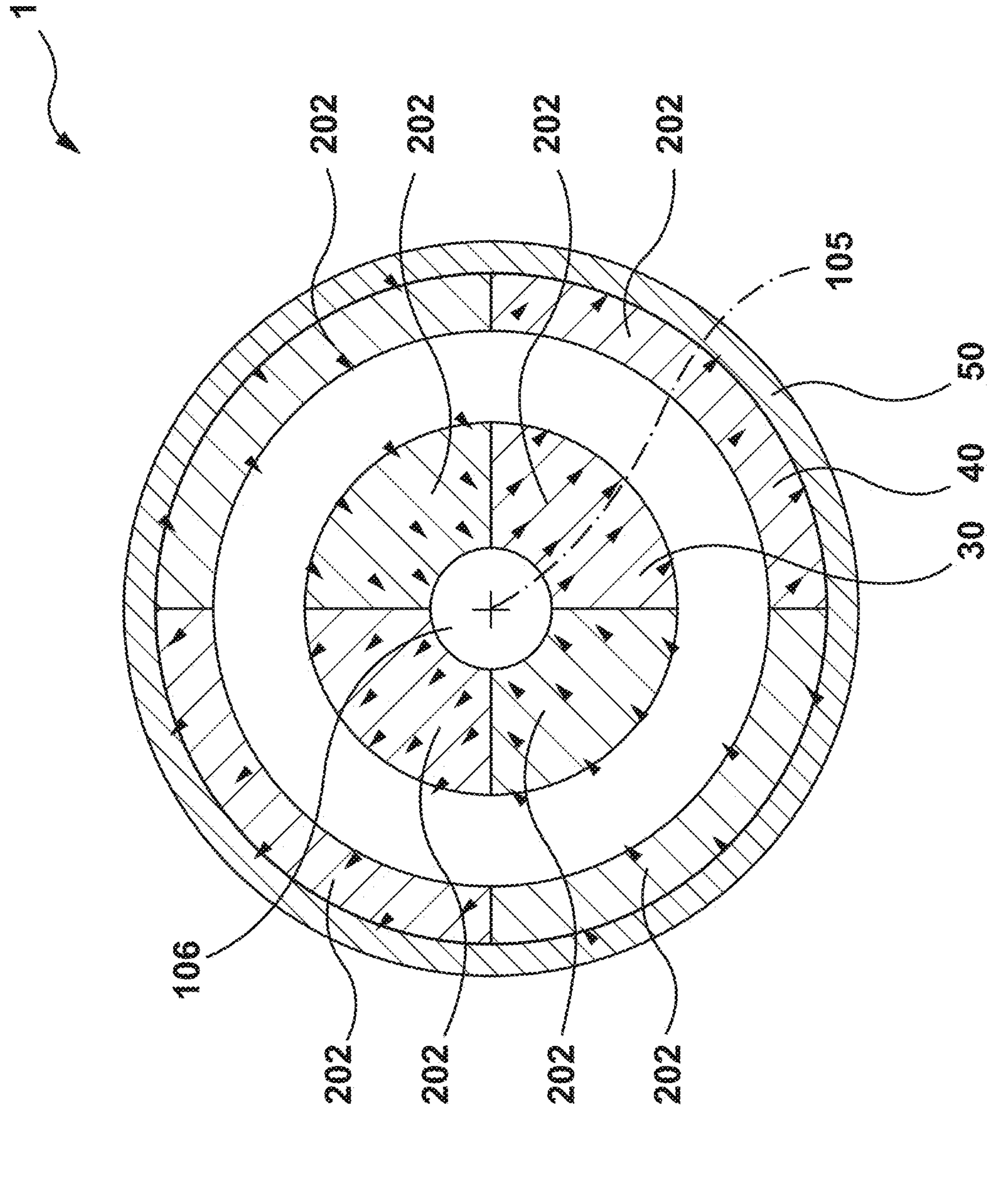
FIG. 2 shows a sectional view through an embodiment of the rotor bearing system according to the invention at a position in which the first permanent magnet, which is mounted in the housing, and the second permanent magnet, which is disposed in the rotor, overlap.

FIG. 2 shows a sectional view of the rotor bearing system 1 at a position in which the first permanent magnet 30, which is mounted in the housing 80, and the second permanent magnet 40, which is disposed in the hollow-cylindrical part 72 of the rotor 70, overlap axially. It can be seen that the first permanent magnet 30 is seated on the shaft 106 which is driven by the motor and is mounted such that it can rotate about the first axis 105. It can also be seen that the second permanent magnet 40 is likewise mounted such that it can rotate about the first axis 105. Both the first permanent magnet 30 and the second permanent magnet 40 comprise two pole pairs, i.e. four poles 202 each, which are respectively radially magnetized as indicated by small arrows.

Figure 3:
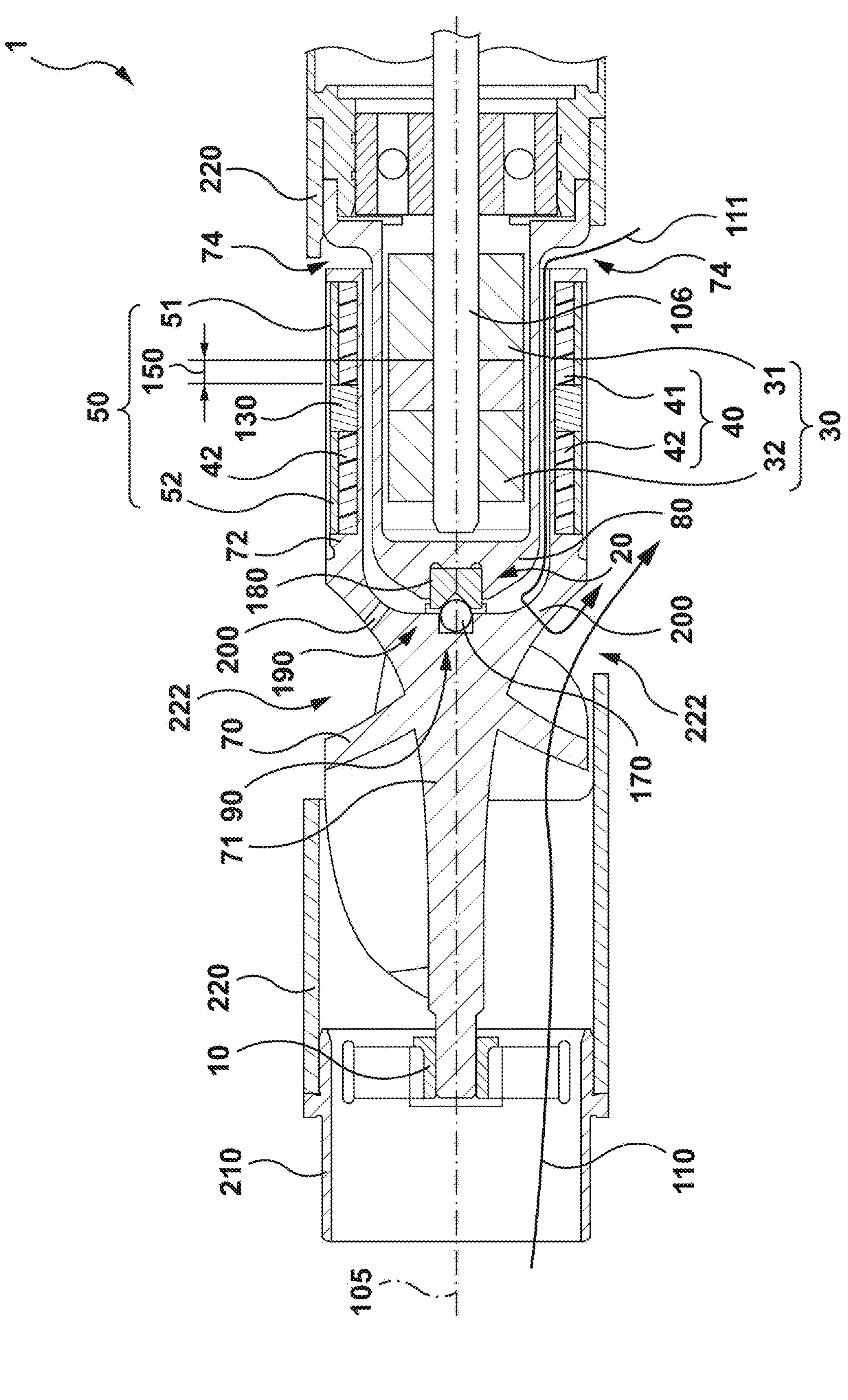
FIGS. 3 and 4 respectively show a rotor bearing system according to further embodiments of the invention.

FIG. 3 shows a rotor bearing system 1 in a similar embodiment as the rotor bearing system 1 of FIG. 1. The present embodiment differs from the embodiment of FIG. 1 in that the first permanent magnet 30, the second permanent magnet 40 and the magnetic return 50 are all divided into two axial segments.

The first permanent magnet 30 comprises the segments 31 and 32, the second permanent magnet 40 comprises the segments 41 and 42, and the magnetic return 50 comprises the segments 51 and 52. The segments 31, 41 and 51 are disposed on the motor side and the segments 32, 42 and 52 are disposed on the side facing the rotor 70.

A hollow-cylindrical and non-magnetic spacer 130, which is likewise mounted on the shaft 106, is disposed between the segments 31 and 32. A further hollow-cylindrical and non-magnetic spacer 130 is disposed between the segments 41 and 51 on the one side and the segments 42 and 52 on the other.

The segmentation in combination with the offset 150 between the two axial halves leads to an increase in the magnetic axial force while, at the same time, the transmittable torque decreases. This measure is taken in the present case because the magnetic axial force is insufficient to reliably compensate the flow force.

Figure 4:
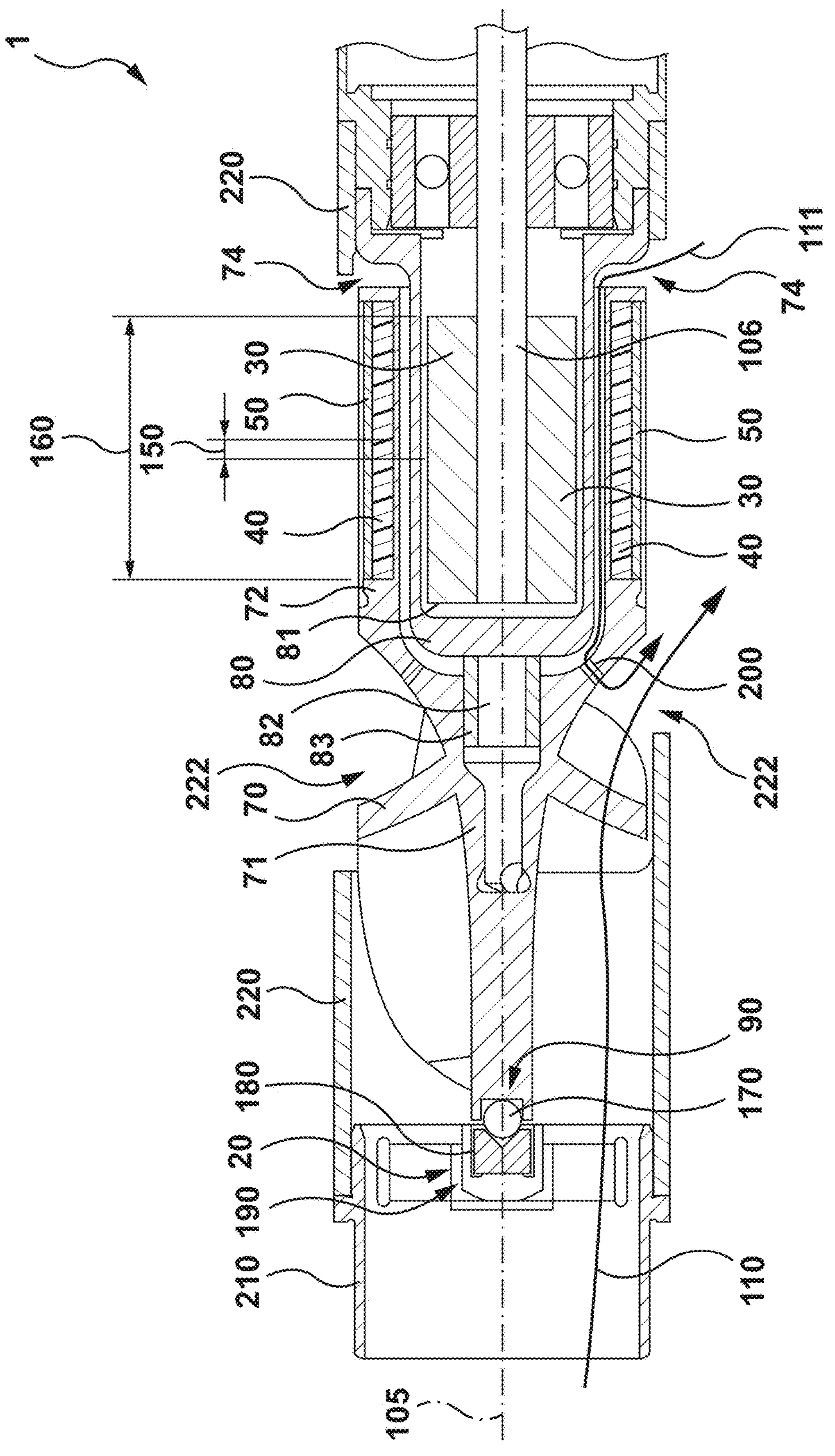

FIG. 4 shows a rotor bearing system 1 in a similar embodiment as the rotor bearing system 1 of FIGS. 1 and 3. The present embodiment differs from the embodiment of FIG. 1 in that, on the one hand, the position of the second bearing 10 is interchanged with the position of the first bearing 20 and the third bearing 90 and, on the other hand, the axial offset 150 between the first permanent magnet 30 and the second permanent magnet 40 points in the opposite direction as in the embodiment of FIG. 1. In the embodiment of FIG. 4, the axial offset 150 is 1 mm.

The first permanent magnet 30 and the second permanent magnet 40 overlap axially at least partially in the axial region identified with the reference sign 160. The first permanent magnet 30 is hereby disposed axially offset relative to the second permanent magnet 40. The centers of the first permanent magnet 30 and the second permanent magnet 40 are marked by vertical dashed lines and the axial offset 150 is drawn in between these two vertical dashed lines. In contrast to the embodiment of FIG. 1, viewed from the housing 80, the first permanent magnet 30 is axially offset relative to the second permanent magnet 40 in the direction of the rotor 70. Between the first permanent magnet 30 and the second permanent magnet 40 in the design example of FIG. 4, there is therefore a defined axial force which acts on the rotor 70 and is directed from the housing 80 toward the rotor 70 along the axis 105; i.e. from right to left in the design example of FIG. 4. A hydraulic force acts on the rotor 70 in the same direction, i.e. likewise from right to left in the design example of FIG. 4.

The advantage of this arrangement is that both the magnetic and the hydraulic axial force on the rotor 70 point in the same direction, namely upstream, as a result of which the rotor 70 is continuously pressed into the combined axial and radial bearing 190.

The first bearing 20 and the third bearing 90 here too form a combined axial and radial bearing 190, which is mounted on the end of the conical part 71 of the rotor 70 facing away from the housing 80. The combined bearing 190 is disposed between the rotor 70 and an insert 210 which is mounted, in particular clamped, on a second housing 220 in an annular end, which is in turn mounted on the housing 80. A ball 170, which is disposed on the end of the conical part 71 of the rotor 70 facing away from the housing, is hereby pressed onto a cone 180 mounted on the insert 210.

The second bearing 10, which is configured as radial, hydrodynamic sliding bearing, is used to receive radial forces and to position the axis of rotation of the second permanent magnet 40, which is disposed in the rotor 70. The second bearing 10 is disposed between the housing 80 and the rotor 70. In contrast to the embodiment of FIG. 1, behind a wall 81 facing toward the rotor 70, the housing 80 of the embodiment of FIG. 4 comprises a cylindrical journal 82 which continues as an extension of the shaft 106 in the direction of the rotor 70. The journal 82 is surrounded by a bearing shell 83 of the radial sliding bearing which forms the second bearing 10.

In summary, the following preferred features of the invention should in particular be noted:

The invention relates to a rotor bearing system 1. Said system comprises a housing 80 in which a first permanent magnet 30 is mounted such that it can rotate about a first axis 105. A rotor 70 for conveying a liquid comprises a second hollow-cylindrical permanent magnet 40, which is mounted such that it can rotate about a second axis. The first permanent magnet 30 and the second permanent magnet 40 overlap axially at least partially, wherein the first permanent magnet 30 is disposed offset relative to the second permanent magnet 40. In the axial overlap region 160 of the first permanent magnet 30 and the second permanent magnet 40, the housing 80 is positioned between the two permanent magnets 30, 40. A first bearing 20 is configured for the relative axial positioning of the rotor 70 and the housing 80 with respect to one another and for receiving an axial force resulting from the arrangement of the first permanent magnet 30 and the second permanent magnet 40, and a second bearing 10 and a third bearing 90 are configured for receiving radial forces and for positioning the axis of rotation of the second permanent magnet 40.

The invention claimed is:

1. A rotor bearing system comprising:

a first permanent magnet configured to rotate about an axis;

a rotor configured to convey a liquid, wherein the rotor comprises a second permanent magnet, wherein the second permanent magnet comprises a hollow permanent magnet and is configured to rotate about the axis;

wherein the first permanent magnet and the second permanent magnet are axially offset and arranged to produce an axial force; and a bearing configured to provide a relative axial positioning of the rotor and the first permanent magnet with respect to one another and configured to receive the axial force resulting from an arrangement of the first permanent magnet and the second permanent magnet, wherein the axial force resulting from the arrangement of the first permanent magnet and the second permanent magnet is configured to be greater than a hydraulic force acting on the rotor.

2. The rotor bearing system of claim 1, wherein the first permanent magnet is mounted within a housing.

3. The rotor bearing system of claim 1, wherein the second permanent magnet is cylindrical.

4. The rotor bearing system of claim 1, wherein the first permanent magnet and the second permanent magnet at least partially overlap axially.

5. The rotor bearing system of claim 4, wherein a housing is positioned between the first permanent magnet and the second permanent magnet in an axial overlap region of the first permanent magnet and the second permanent magnet.

6. The rotor bearing system of claim 1, further comprising a second bearing, wherein the bearing and the second bearing are configured to receive radial forces and configured to position the axis of rotation of the second permanent magnet.

7. The rotor bearing system of claim 6, wherein the bearing is disposed between the first permanent magnet and the rotor and the second bearing is disposed on the rotor.

8. The rotor bearing system of claim 1, wherein each of the first permanent magnet and the second permanent magnet comprise at least one pair of poles, wherein the first permanent magnet and the second permanent magnet comprise an equal number of pairs of poles.

9. A heart support system comprising:

a rotor bearing system comprising:

a first permanent magnet configured to rotate about an axis;

a rotor configured to convey a liquid, wherein the rotor comprises a second permanent magnet, wherein the second permanent magnet comprises a hollow permanent magnet and is configured to rotate about the axis;

wherein the first permanent magnet and the second permanent magnet are axially offset and arranged to produce an axial force; and a bearing configured to provide a relative axial positioning of the rotor and the first permanent magnet with respect to one another and configured to receive the axial force resulting from an arrangement of the first permanent magnet and the second permanent magnet, wherein the axial force resulting from the arrangement of the first permanent magnet and the second permanent magnet is configured to be greater than a hydraulic force acting on the rotor.

10. The heart support system of claim 9, wherein the first permanent magnet is mounted within a housing.

11. The heart support system of claim 9, wherein the second permanent magnet is cylindrical.

12. The heart support system of claim 9, wherein the first permanent magnet and the second permanent magnet at least partially overlap axially.

13. The heart support system of claim 12, wherein a housing is positioned between the first permanent magnet and the second permanent magnet in an axial overlap region of the first permanent magnet and the second permanent magnet.

14. The heart support system of claim 9, further comprising a second bearing, wherein the bearing and the second bearing are configured to receive radial forces and configured to position the axis of rotation of the second permanent magnet.

15. The heart support system of claim 14, wherein the bearing is disposed between the first permanent magnet and the rotor and the second bearing is disposed on the rotor.

16. The heart support system of claim 9, wherein each of the first permanent magnet and the second permanent magnet comprise at least one pair of poles, wherein the first permanent magnet and the second permanent magnet comprise an equal number of pairs of poles.

* * * * *